(12) United States Patent
Woltermann

(10) Patent No.: US 11,383,082 B2
(45) Date of Patent: Jul. 12, 2022

(54) FORMULATING, TRACKING, DISPLAYING, AND USING ELECTRICAL MUSCLE STIMULATION (EMS) INTENSITY VALUES

(71) Applicant: Katalyst Inc., Tumwater, WA (US)

(72) Inventor: Björn Erich Woltermann, Seattle, WA (US)

(73) Assignee: Katalyst Inc., Tumwater, WA (US)

(*) Notice: Subject to any disclaimer, the term of this patent is extended or adjusted under 35 U.S.C. 154(b) by 153 days.

(21) Appl. No.: 16/912,382

(22) Filed: Jun. 25, 2020

(65) Prior Publication Data

US 2021/0402180 A1    Dec. 30, 2021

(51) Int. Cl.
| | |
|---|---|
| A61N 1/36 | (2006.01) |
| A61N 1/04 | (2006.01) |
| G05B 19/042 | (2006.01) |
| G16H 20/30 | (2018.01) |

(52) U.S. Cl.
CPC ....... *A61N 1/36003* (2013.01); *A61N 1/0452* (2013.01); *A61N 1/0484* (2013.01); *A61N 1/36034* (2017.08); *G05B 19/042* (2013.01); *G16H 20/30* (2018.01); *G05B 2219/23258* (2013.01)

(58) Field of Classification Search
CPC ............... A61N 1/0452; A61N 1/0484; A61N 1/36003; A61N 1/36034; G05B 19/042; G05B 2219/23258; G16H 20/30; G16H 40/60; G16H 40/63; G16H 40/67; A63B 24/00; A61H 1/0262; A61H 1/0274; A61H 2201/10; A61H 2201/1261; A61H 2201/5043

USPC .......................................................... 607/43
See application file for complete search history.

(56) References Cited

U.S. PATENT DOCUMENTS

| | | | |
|---|---|---|---|
| 5,961,542 A | 10/1999 | Agarwala | |
| 2004/0147975 A1 | 7/2004 | Popovic et al. | |
| 2016/0303363 A1* | 10/2016 | Girouard | ............ A61N 1/36003 |
| 2018/0036531 A1* | 2/2018 | Schwarz | ................ G16H 20/30 |
| 2018/0304074 A1* | 10/2018 | Matsushita | .......... A61N 1/3603 |
| 2019/0083029 A1 | 3/2019 | Buhlmann et al. | |
| 2019/0159959 A1 | 5/2019 | Smith | |

(Continued)

OTHER PUBLICATIONS

The International Search Report and Written Opinion for PCT Application No. PCT/US21/38749, dated Oct. 19, 2021.

*Primary Examiner* — Carl H Layno
*Assistant Examiner* — Jane C Kalinock
(74) *Attorney, Agent, or Firm* — Lee & Hayes, P.C.

(57) ABSTRACT

Described herein are techniques, devices, and systems for formulating, tracking, displaying, and using electrical muscle stimulation (EMS) intensity values that are meaningful and intuitive. Electrical impulses may be delivered via multiple electrodes of an EMS suit in accordance with pulse intensity settings, the pulse intensity settings comprising multiple channel intensity values associated with multiple channels. Each channel intensity value can be multiplied by a predefined number to generate displayable channel intensity values, and a global intensity value can be derived from the displayable channel intensity values. The global intensity value can be presented on a display, such as by presenting the global intensity value as a graphic overlaying media content featuring an instructor conducting a workout session.

20 Claims, 15 Drawing Sheets

(56) References Cited

U.S. PATENT DOCUMENTS

2019/0388683 A1  12/2019  Chen
2020/0230405 A1* 7/2020  Chun ................. A63B 21/0054

* cited by examiner

FORMULATING, TRACKING, DISPLAYING, AND USING ELECTRICAL MUSCLE STIMULATION (EMS) INTENSITY VALUES

BACKGROUND

Electrical Muscle Stimulation (EMS) is a technology that elicits muscle contraction using electrical impulses. The impulses are delivered via electrodes placed on the body near the muscles that are to be stimulated. EMS technology has been used to develop fitness products, such as EMS suits, which are designed to help users achieve their health and fitness goals, whether the goal is to increase muscle activation, improve muscle tone, increase strength, and/or recover from an injury. When a user wears an EMS suit, the electrodes in the suit are situated near particular muscles groups (e.g., arms, legs, chest, abdominals, back, etc.) in order to deliver electrical impulses targeted to those muscle groups while the user performs various exercise movements. Existing EMS suits deliver electrical impulses via channels, each channel corresponding to a pair of electrodes. For example, Channel 1 might correspond to an electrode pair on a first muscle group, Channel 2 might correspond to an electrode pair on a second muscle group, Channel 3 might correspond to an electrode pair on a third muscle group, and so on and so forth.

In general, the intensity (or amplitude) at which electrical impulses are delivered on each channel is adjustable. This serves the purpose of providing an appropriate amount of electrical current to the user's muscles, and it also allows for progressively increasing the intensity throughout a curated workout session. In order to provide feedback to the user regarding the intensity, existing EMS systems often display one or more numbers that are intended to represent the intensity at which the electrical impulses are being delivered at any given moment. However, these numbers are not intuitive or meaningful because they do not provide a good indication of the actual intensity of the electrical impulses that are being delivered. For example, a display of an existing EMS system might present multiple channel intensity values for multiple channels of an EMS suit, each channel intensity value being a number between 0 and 100, and/or the display might present a master intensity value that is also a number between 0 and 100. Although a user of such a system may intuit that decreasing one of these numbers will cause electrical current to decrease (on one channel or across multiple channels), and that increasing one of these numbers will cause electrical current to increase (on one channel or across multiple channels), the user is nevertheless unable to make sense of the actual intensity of the electrical impulses delivered via any given channel using this system. In other words, a channel intensity value of 100 in this existing system does not necessarily mean that electrical current on that channel is being delivered at a maximum intensity. This can be because the actual intensity of the electrical impulses delivered via any given channel is often calculated as a function of both the channel intensity value and the master intensity value, such as using Equation (1), below:

$$\text{Master}(0 \text{ to } 100\%) \times \text{Channel}_{1 \text{ to } N}(0 \text{ to } 100\%) \times \text{Max} \cdot \text{Channel Intensity} = \text{Channel Intensity}_{1 \text{ to } N} \quad (1)$$

To illustrate, a first user (User A) wearing a first EMS suit might see, on User A's display, Master=50 and/or Channel 1=50. Using Equation (1), and assuming a maximum channel intensity of 120 milliamps (mA), the actual intensity of the electrical impulses being delivered on Channel 1 for User A is calculated as 30 mA. Meanwhile, a second user (User B) wearing a second EMS suit might see, on User B's display, Master=100 and/or Channel 1=25. Using Equation (1), and assuming the same maximum channel intensity of 120 mA, the actual intensity of the electrical impulses being delivered on Channel 1 for User B is also calculated as 30 mA, even though different intensity values are displayed to User A and User B. One can readily appreciate that these intensity value examples (e.g., Master=50 and/or Channel 1=50 for User A; Master=100 and/or Channel 1=25 for User B) are not intuitive or meaningful to the users, which makes it difficult for the users to figure out how to adjust the intensity settings to deliver electrical impulses at an appropriate and/or desired intensity. Even an experienced trainer may have difficulty using such an EMS system.

Another drawback of existing EMS systems is that they only store (e.g., on a chip card) a point-in-time snapshot of the ending channel intensities of electrical impulses that were delivered at the very end of a workout session. These ending intensities are often used to determine starting intensities of electrical impulses for a subsequent workout session. However, without knowing a full history of how (in terms of intensity adjustments) a given user progressed through a workout session from start-to-finish, these starting intensities may be ill-suited for a given user. In other words, if an algorithm is tasked with determining starting intensities for an upcoming workout session, and if the only information available to make that determination is a single array of channel intensities that were output via an EMS suit at the very end of a previous workout session, the next workout session may be initiated at an inappropriate starting intensity.

Discussed herein are technological improvements for, among other things, these devices and systems.

BRIEF DESCRIPTION OF THE DRAWINGS

The detailed description is described with reference to the accompanying figures. In the figures, the left-most digit(s) of a reference number identifies the figure in which the reference number first appears. The same reference numbers in different figures indicate similar or identical items.

FIG. 6 also illustrates flow diagram of an example process for determining a performance score and/or a starting intensity for a next workout session based on the area under the curve.

DETAILED DESCRIPTION

Figure 1:
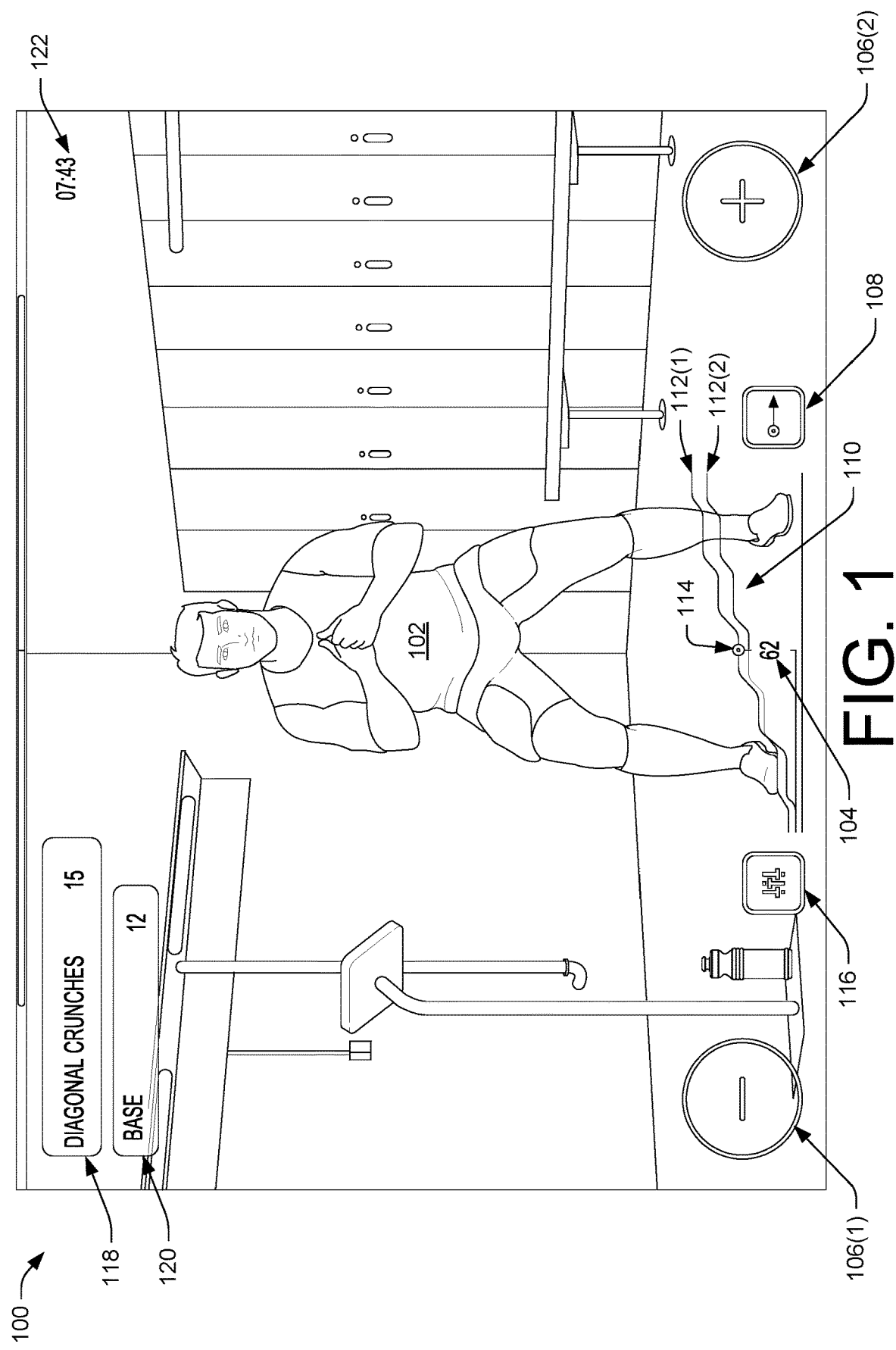
FIG. 1 is an example graphical user interface (GUI) that may be presented on a display to a user, such as a user of an EMS suit. The example GUI may present, among other things, an adjustable global intensity value that is derived from channel intensity values.

This disclosure is directed to, among other things, techniques, devices, and systems for formulating, tracking, displaying, and using electrical muscle stimulation (EMS) intensity values that are meaningful and intuitive. An example system for implementing the techniques described herein may include a processor(s), a display(s), memory storing pulse parameter settings, and an EMS suit having multiple electrodes, wherein individual pairs of the multiple electrodes correspond to individual channels of multiple channels for delivering electrical impulses via the multiple electrodes. For example, the electrodes of the EMS suit are controllable by the processor(s) to deliver electrical impulses to muscles of a user who is wearing the EMS suit in order to elicit muscle contraction. When an electrical impulse is delivered via a pair of electrodes, electrical current (i.e., the flow of charged particles) flows from one electrode (of the pair), through a portion of the user's body (e.g., through muscle tissue underlying the pair of electrodes), and to the other electrode (of the pair). The user's body completes an electrical circuit that includes the pair of electrodes, thereby allowing electrical current to flow between the pair of electrodes during operation of the EMS suit, as electrical impulses are delivered via the electrodes. As used herein, a "pair" of electrodes can mean two electrodes that correspond to a common channel of multiple channels that are used to deliver electrical impulses, channel-by-channel, during operation of the EMS suit. A "pair" of electrodes can also mean two electrodes that allow for electrical current to flow therebetween during operation of the EMS suit, one electrode of the pair operating as a positive electrode (anode) and the other electrode of the pair operating as a negative electrode (cathode). It is to be appreciated that, with alternating current (AC), each electrode of a given pair reverses current with each cycle (or frame). That is, each electrode may change from a positive electrode (anode) to a negative electrode (cathode) with each cycle (or frame).

In general, the electrodes of the EMS suit are arranged in/on the EMS suit to cover parts of the user's body in order to excite particular muscle groups (e.g., arms, legs, chest, abdominals, back, etc.) through the delivery of electrical impulses that stimulate the muscle tissue beneath the user's skin. The EMS suit described herein is configured to deliver electrical impulses via multiple electrodes of the EMS suit over a series of frames, where pulses are delivered channel-by-channel during a given frame in accordance with pulse parameter setting, which may include, among other types of settings, pulse intensity settings. That is, the intensities of the electrical impulses are controllable using channel-specific (or muscle-group-specific) pulse intensity settings. A channel-specific pulse intensity setting may represent an intensity (or amplitude) of an electrical pulse delivered via a specific channel of a multi-channel EMS suit. Each channel's pulse intensity can be set independently of the other channels at an appropriate channel intensity value. For example, a processor(s) may cause delivery of an electrical pulse via Channel 1 (e.g., abdominals) at a channel intensity value of 20 milliamps (mA), may cause delivery of an electrical pulse via Channel 2 (e.g., left arm) at a channel intensity value of 15 mA, and may cause delivery of an electrical pulse via Channel 3 (e.g., quadriceps) at a channel intensity value of 40 mA, and so on and so forth, for any suitable number of channels.

Disclosed herein are techniques for formulating displayable intensity values that are meaningful and intuitive to users. In an illustrative example, each of the aforementioned channel intensity values in the pulse intensity settings may be multiplied by a predefined number to generate a plurality of displayable channel intensity values (sometimes referred to herein as "channel-specific intensity values"). In addition, one or more channel subset intensity values can be derived from subsets of the channels, and a global intensity value can be derived from the complete set of displayable channel intensity values. In some embodiments, at least the global intensity value can be presented on a display to provide feedback to the user regarding the intensity of the electrical impulses being delivered via the electrodes of an EMS suit the user is wearing. Notably, this global intensity value is meaningful and intuitive to the user due to the way it is formulated; the global intensity value is derived from the displayable channel intensity values, which, in turn, are generated based on the actual channel intensity values in the pulse intensity settings, which may be expressed as numbers of milliamps, for example.

An example process, in accordance with embodiments described herein, may include delivering electrical impulses via multiple electrodes of an EMS suit in accordance with pulse intensity settings, the pulse intensity settings comprising multiple channel intensity values associated with multiple channels, multiplying each channel intensity value of the multiple channel intensity values by a predefined number to generate displayable channel intensity values, deriving a global intensity value from the displayable channel intensity values, and presenting the global intensity value on a display. In some embodiments, the global intensity value may be presented on the display as a graphic overlaying media content featuring an instructor conducting a workout session. For example, a user of the EMS suit may be conducting a workout session by following along with movements of an instructor depicted in media content output on a display.

By formulating intensity values that are meaningful and intuitive, a user who is presented with one or more of such intensity value on a display may be provided with intensity-related feedback that the user can readily understand in order to be adequately informed of the intensity of the output being provided by his/her EMS suit. In turn, the user may better understand how to adjust the intensity of output. The result is an EMS system that is easy to use from a standpoint of understanding and adjusting the intensity of output. These intensity values may also be stored (or tracked) as the EMS suit is operating by controlling the delivery of electrical impulses via electrodes in accordance with the pulse intensity settings. A more standardized approach to formulating displayable intensity values allows for generating comparisons of workout sessions, such as comparing a current workout session to a previous workout session(s) of the same user, and/or generating comparisons of workout sessions across multiple users (e.g., friends, social network connections, trainers, professional athletes, etc.). Also disclosed herein are gamification techniques to help keep users engaged with the EMS system and wanting to use their EMS suit more frequently. Also disclosed herein are improvements in curating workout sessions, such as by determining starting intensity values of an upcoming workout session that are better suited to the individual user.

The techniques and systems described herein may also allow for one or more devices to conserve resources with respect to communications bandwidth resources, processing resources, memory resources, power resources, and/or other resources, as described herein. Additional technical effects can also be realized from an implementation of the technologies disclosed herein. Described herein are example processes, as well as systems and devices comprising one or more processors and one or more memories, as well as non-transitory computer-readable media storing computer-executable instructions that, when executed, by one or more processors perform various acts and/or processes disclosed herein.

FIG. 1 is an example graphical user interface (GUI) 100 that may be presented on a display to a user, such as a user wearing an EMS suit that is being controlled by a processor(s) for delivering electrical impulses via electrodes of the EMS suit. The GUI 100 may be presented on any suitable display, such as a display of a computing device (e.g., a tablet computer, a mobile phone, wearable computer, etc.) that is playing media content featuring an instructor conducting a workout session, a peripheral display system to which the media content is casted, a display on the EMS suit itself, etc. In general, and regardless of the display on which it is presented, the GUI 100 may represent visual information that the user can view during a workout session, while wearing and operating an EMS suit.

In general, the GUIs described herein may present various elements based on code or computer-executable instructions executed on a computing device. In the GUIs described herein, at least some of the presented elements may be selectable for providing an interactive GUI. For example, the user may interact with the GUI via touch-based user input (e.g., the user may select elements by touching the display at locations where the elements are displayed). To enable this type of interaction, the GUI may be displayed on a display that functions as a touch screen (e.g., a capacitive-based touchscreen, or any other type of touchscreen technology). Additionally, or alternatively, a user may interact with the GUI using other types of user input besides touch, such as voice-based user input (e.g., the user may utter voice commands that are processed using automatic speech recognition (ASR) and/or natural language understanding (NLU) software), gestural user input (e.g., the user may wave a hand in a particular direction or motion, the user may make a "thumbs-up" gesture or a "thumbs-down" gesture with a hand, etc.), or any other type of user input known to a person having ordinary skill in the art. Gestural user input, for example, may be detectable using a camera that is oriented toward the user who is providing the user input (e.g., a front facing camera of a tablet computer), and using associated image processing software to process the images for gesture detection.

As shown in FIG. 1, the GUI 100 may include various graphical elements overlaying media content 102. The media content 102 may be output on a display based on corresponding media data (e.g., a video file(s)) that is being played back on a computing device. For example, the user may download or stream media data (e.g., a video file) over a computer network to a computing device, and when this media data is played on the computing device, media content 102 (e.g., video frames) may be output on a display of the computing device for viewing consumption by the user. The example media content 102 shown in FIG. 1 features an instructor performing a workout session. A user wearing an EMS suit may wish to follow along with the instructions of the instructor, which may include both visual cues and verbal instructions/commands to help guide the user through a workout session.

The graphical elements of the GUI 100 shown in FIG. 1 may include an adjustable global intensity value 104. In the example of FIG. 1, the global intensity value 104 is currently set to a value of "62". As will be described in more detail below, pulse intensity settings across multiple channels of an EMS suit may be comprised of multiple channel intensity values, such as the number of milliamps (mA) of the electrical impulses being delivered on each channel of the EMS suit. In order to formulate the global intensity value 104, each channel intensity value can be multiplied by a predefined number (e.g., the number 3, 4, 5, etc.) to generate displayable channel intensity values. The global intensity value 104 may be derived from these displayable channel intensity values, such as by computing the average of the displayable channel intensity values. Although the global intensity value 104 is often described as the average of the displayable channel intensity values, it is to be appreciated that the global intensity value 104 can be computed or calculated as any suitable statistical value (e.g., mean, median, mode, etc.) based on the displayable channel intensity values. In the example of FIG. 1, the average of the displayable channel intensity values may equal 62, which is why the global intensity value 104 is formulated as the value "62" and presented via the GUI 100. In a simple example, consider a scenario where all of the channels of the EMS suit are set to a channel intensity value of 15.5 mA. This value may be multiplied by a predefined number (e.g., the number 4) to generate a displayable channel intensity value of "62" for each channel. Since the average of the displayable channel intensity values across the multiple channels is "62", the global intensity value 104 may be formulated as the number "62."

The graphical elements of the GUI 100 shown in FIG. 1 may further include a first intensity adjustment control 106(1) (e.g., a "minus" icon) and a second intensity adjustment control 106(2) (e.g., a "plus" icon). In the state of the GUI 100 shown in FIG. 1—where individual channels, or subsets of channels, are not currently displayed for adjustment—these intensity adjustment controls 106 may be utilized to adjust (e.g., increase or decrease) the global intensity value 104. For example, the first intensity adjustment control 106(1), upon selection, may decrease the global intensity value 104 from a current value (e.g., "62" in FIG. 1) to a decreased value (e.g., "61"), and the second intensity adjustment control 106(2), upon selection, may increase the global intensity value 104 from a current value (e.g., "62" in FIG. 1) to an increased value (e.g., "63"). In some embodiments, an individual selection (e.g., touch) of the first intensity adjustment control 106(1) may decrement the global intensity value 104 by one (e.g., from "62" to "61"), and an individual selection (e.g., touch) of the second intensity adjustment control 106(2) may increment the global intensity value 104 by one (e.g., from "62" to "63"). However, the system may adjust the global intensity value 104 by more than one with each selection of an intensity adjustment control 106, in some embodiments. In some embodiments, a "touch-and-hold" type of user input detected on either of the intensity adjustment controls 106 may cause the global intensity value 104 to continue adjusting until the user ceases touching the intensity adjustment control 106, and the rate at which the adjustment occurs may gradually increase the longer the user holds the touch-based input on the intensity adjustment control 106.

If the user selects one of the intensity adjustment controls 106 to adjust the global intensity value 104, logic of the system may determine, based on the adjusted global intensity value 104, respective amounts by which to adjust respective ones of the multiple channel intensity values. Continuing with the running example, if all of the channels are set to the same channel intensity value (e.g., 15.5 mA), an adjustment of the global intensity value 104 from "62" to "63" may cause adjustment of each displayable channel intensity value by the same amount (i.e., from "62" to "63"), and each channel intensity value in the pulse intensity settings may be commonly adjusted (e.g., from 15.5 mA to 15.75 mA). After this adjustment, electrical impulses may be delivered at the new channel intensity values of 15.75 mA, and the adjusted global intensity value 104 (e.g., "63") may be presented on a display via the GUI 100.

As mentioned above, other forms of user input may be provided to adjust the global intensity value 104 in a similar manner, such as by uttering voice commands (e.g., the user may utter: "increase the intensity", "decrease the intensity", etc.). In some embodiments, a voice command may be issued to adjust the global intensity value 104 to a targeted number (e.g., the user may utter: "change the intensity to 68"). As another example, the user may form a "thumbs-up" gesture with his/her hand that is captured via a camera and processed by image processing software to interpret the gesture as a command to increase the global intensity value 104.

Figure 4A:
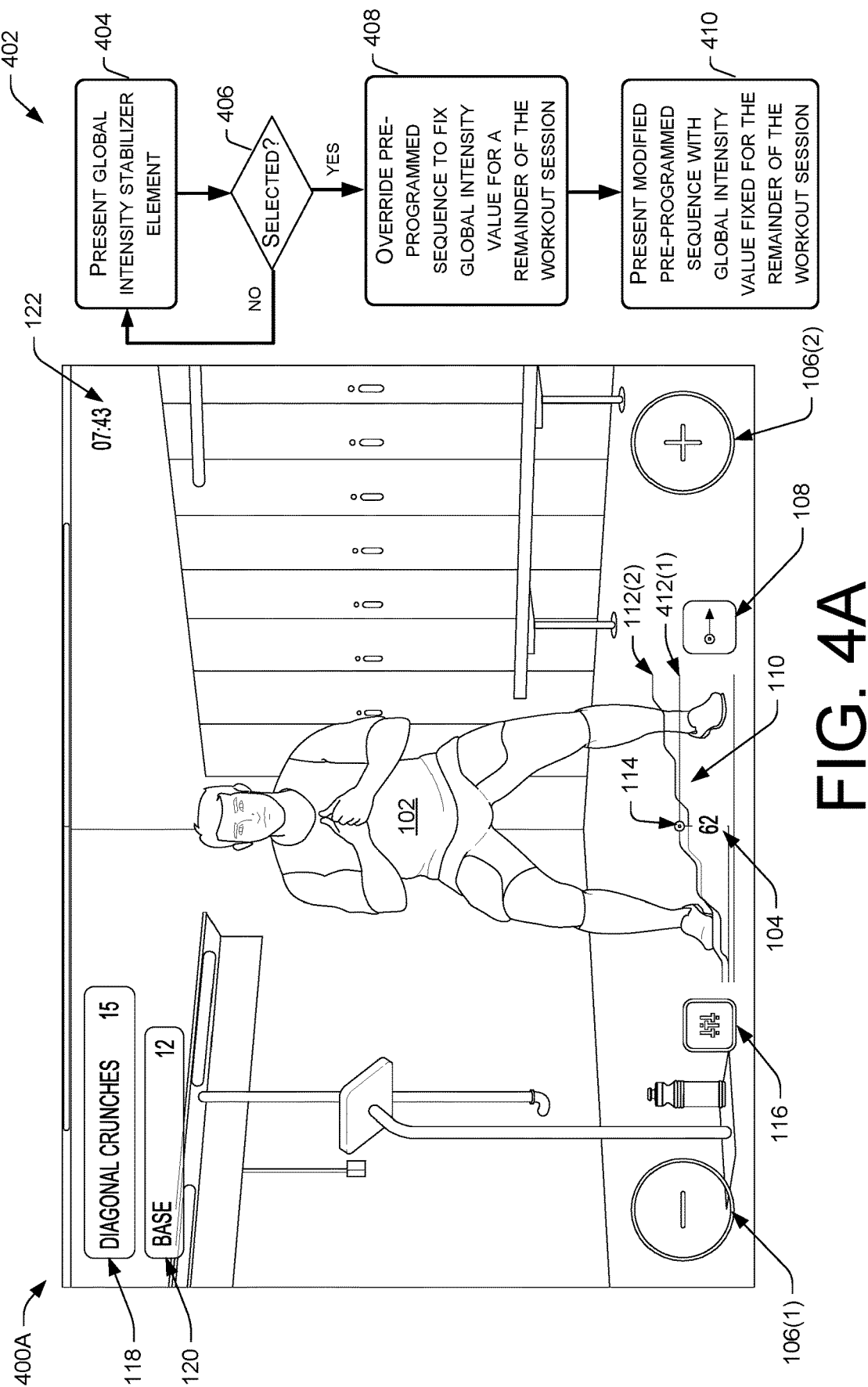
FIG. 4A is an example of a GUI that may be presented on a display, and a flow diagram of an example process for presenting the GUI. The example GUI of FIG. 4A may be presented after user selection of a selectable element presented in the example GUI shown in FIG. 1. The example GUI of FIG. 4A illustrates how the user may fix the global intensity value for a remainder of a workout session.

The graphical elements of the GUI 100 shown in FIG. 1 may further include a global intensity stabilizer element 108 that, upon selection, causes the global intensity value 104 to remain fixed at a current value for the remainder of a workout session, and this may be depicted on a graph 110, as shown in FIG. 4A, which will be described in more detail below. FIG. 1 shows a state of the GUI 100 prior to selection of the global intensity stabilizer element 108, where a graph 110 is presented via the GUI 100 near the global intensity value 104. The graph 110 may depict a pre-programmed sequence of global intensity values plotted over time, a history of global intensity values plotted over time, and/or a combination thereof. In some embodiments, the graph 110 may show multiple histories of global intensity values for comparison. In FIG. 1, the graph 110 is showing two curves 112(1) and 112(2). A first curve 112(1) may represent a combination of a pre-programmed sequence of global intensity values and a history of global intensity values, these values being associated with a current workout session in which the user who is wearing the EMS suit is currently engaged. For example, an element 114 on the first curve 112(1) may indicate a progress of the user towards completion of the current workout session, and the history of global intensity values is plotted behind (e.g., to the left of) the element 114 to represent an intensity profile associated with the user for the already-completed portion of the workout session. A pre-programmed sequence of global intensity values may be plotted in front of (e.g., to the right of) the element 114 to represent predicted global intensity values that are predicted to be plotted on the graph 110 for a to-be-completed portion of the workout session, assuming that the user progresses through the workout session in a manner that the user is predicted to progress through the workout session. The second curve 112(2) shown on the graph 110 may represent a history of global intensity values associated with another workout session that is different from the current workout session associated with the user who is wearing the EMS suit and viewing the media content 102. For example, the second curve 112(2) may be associated with a previous workout session that the user has already completed, or the second curve 112(2) may be associated with a workout session that was performed, or is being performed, by another user (e.g., a friend or social connection of the user, the instructor depicted in the media content 102, a celebrity (e.g., a professional athlete), etc.). Accordingly, the presentation of the graph 110 via the GUI 100 may allow a user to compare the user's current performance to the user's own past performance, and/or to a past or current performance of another user. This not only provides feedback to the user regarding the user's performance, but it also provides gamification features that help to keep the user engaged with the EMS system described herein.

Figure 4B:
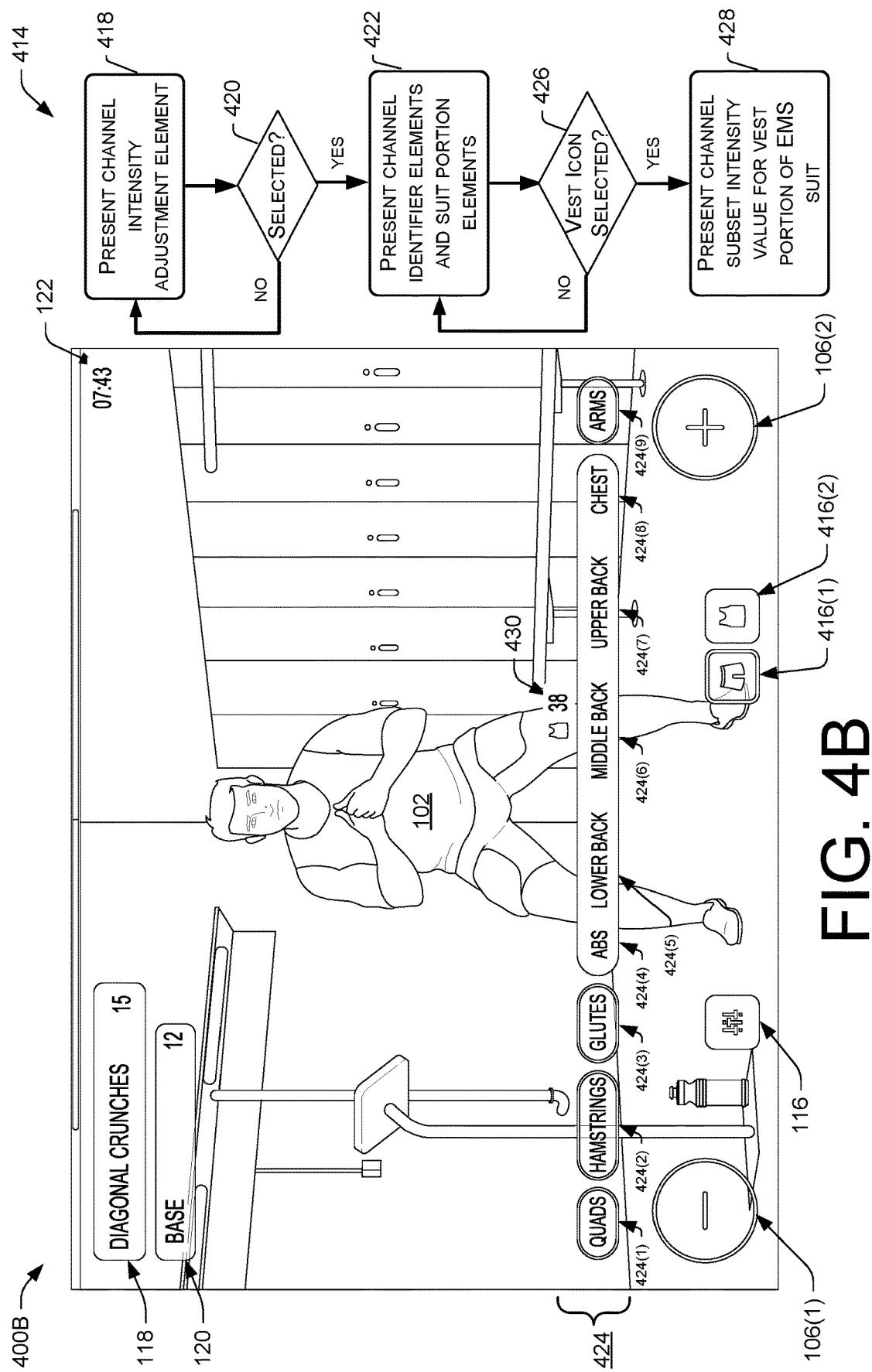
FIG. 4B is another example of a GUI that may be presented on a display, and a flow diagram of an example process for presenting the GUI. The example GUI of FIG. 4B may be presented after user selection of a selectable element presented in the example GUI shown in FIG. 1, and after selection of a "vest" icon that is presented after the user selection of the selectable element. The example GUI of FIG. 4B illustrates how a user can adjust an intensity value associated with the vest portion of the EMS suit.
Figure 4C:
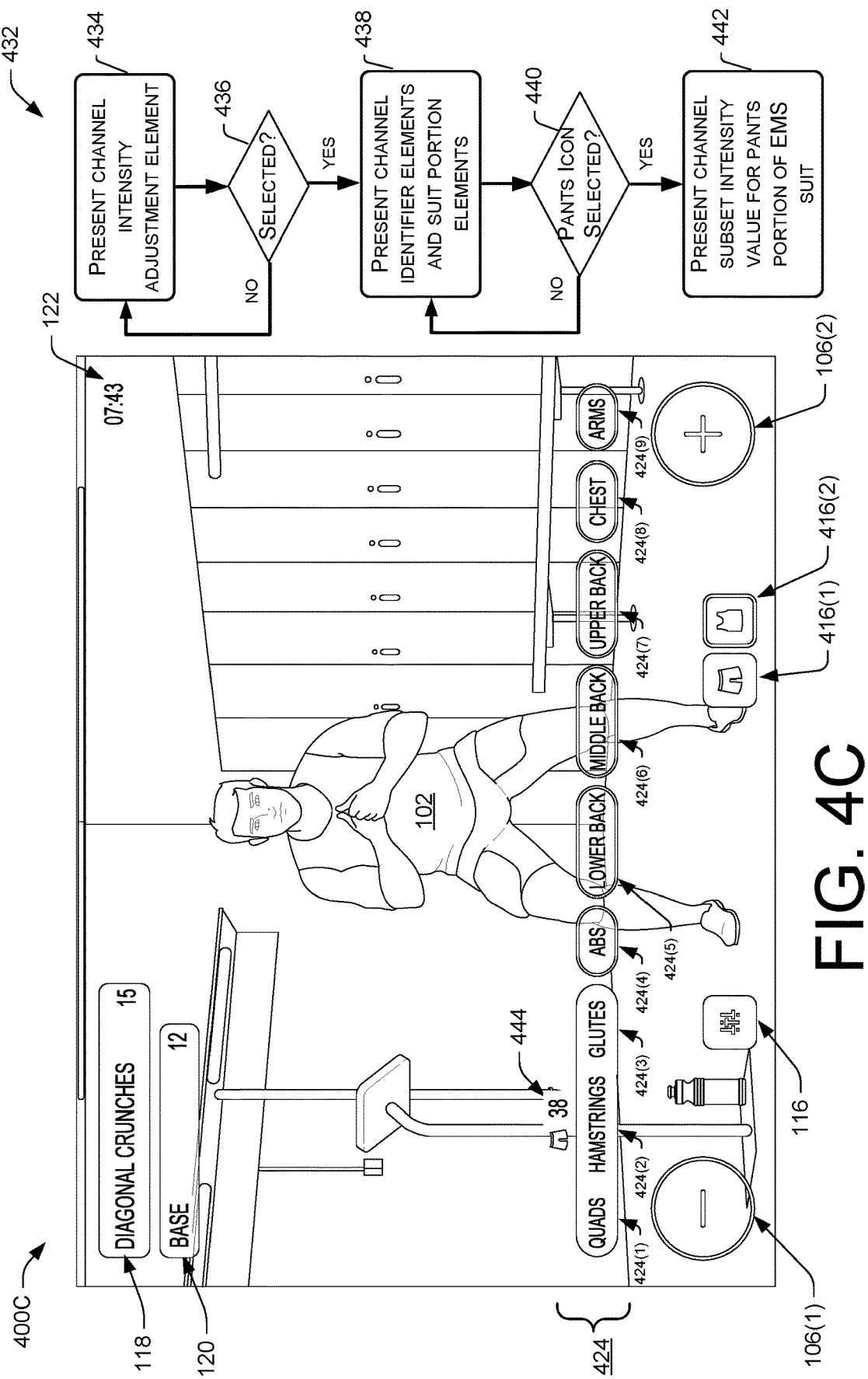
FIG. 4C is another example of a GUI that may be presented on a display, and a flow diagram of an example process for presenting the GUI. The example GUI of FIG. 4C may be presented after user selection of a selectable element presented in the example GUI shown in FIG. 1, and after selection of a "pants" icon that is presented after the user selection of the selectable element. The example GUI of FIG. 4C illustrates how a user can adjust an intensity value associated with the pants portion of the EMS suit.
Figure 4D:
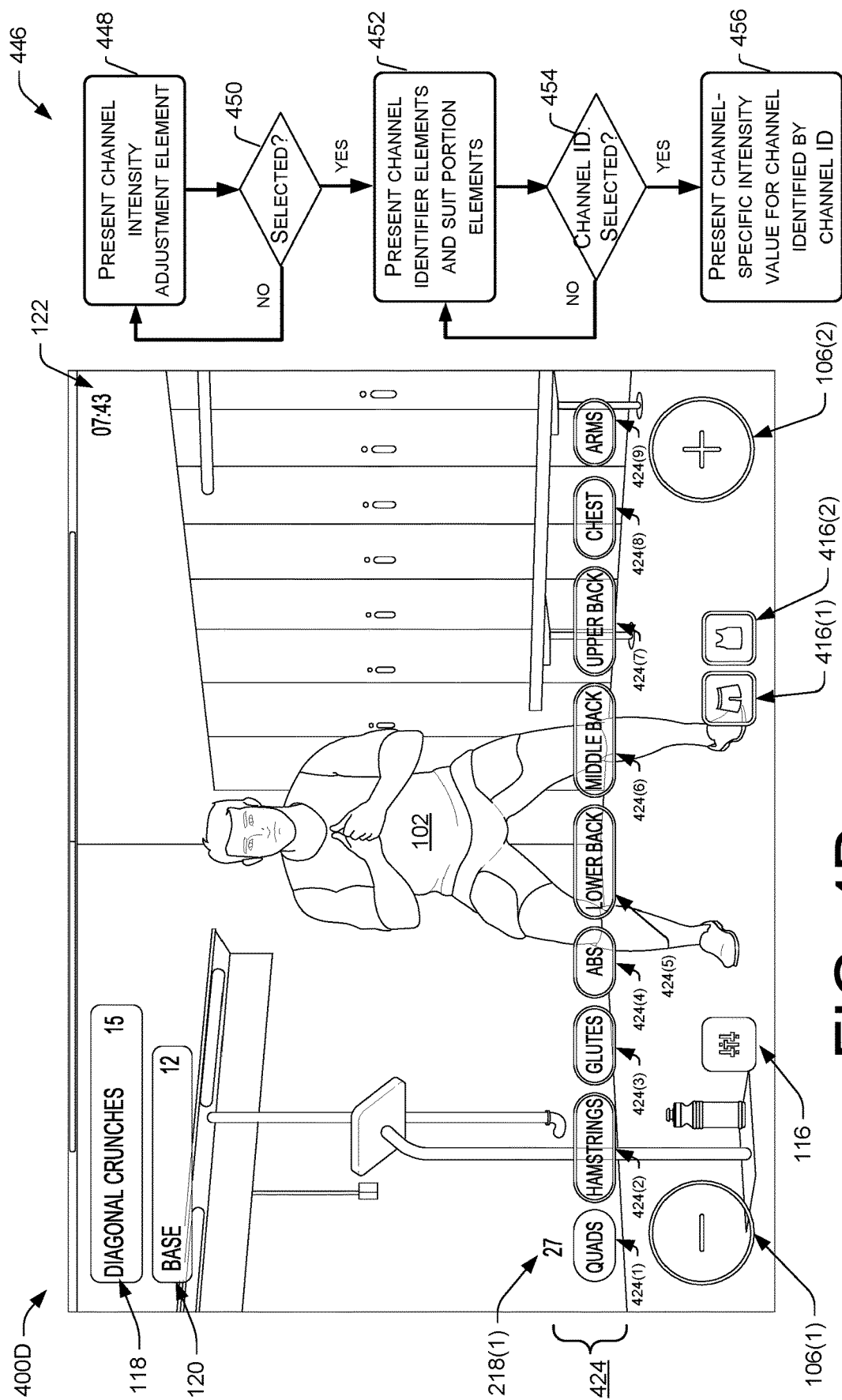
FIG. 4D is another example of a GUI that may be presented on a display, and a flow diagram of an example process for presenting the GUI. The example GUI of FIG. 4D may be presented after user selection of a selectable element presented in the example GUI shown in FIG. 1, and after selection of a channel icon that is presented after the user selection of the selectable element. The example GUI of FIG. 4D illustrates how a user can adjust an intensity value associated with an individual channel of the EMS suit.

The graphical elements of the GUI 100 shown in FIG. 1 may further include a channel intensity adjustment element 116 that, upon selection, presents channel identifier elements (e.g., names) corresponding to the channels of the EMS suit, which, in turn, allows for adjusting intensity of electrical impulses delivered via individual channels, or subsets of channels. These sub-level intensity adjustment features are shown in FIGS. 4B-4D, and will be described in more detail with reference to at least those figures.

The graphical elements of the GUI 100 shown in FIG. 1 may further include additional graphical overlays that may be presented persistently or at appropriate times during presentation of the media content 102 to convey certain information, such as the name of the current exercise movement 118. In the example GUI 100, the name of the current exercise movement 118 (e.g., "Diagonal Crunches") may be prominently displayed (e.g., bolded, highlighted, relatively large, at a top of the display, and/or above other names of exercise movements, etc.) via the GUI 100. Meanwhile, the names of past or upcoming exercise movements 120 may also be displayed, but perhaps less prominently (e.g., grayed out, relatively small, below the name of the current exercise movement 118, and/or at least partially behind other elements of the GUI 100, etc.).

The graphical elements of the GUI 100 shown in FIG. 1 may further include time information 122 (e.g., a countdown to the initiation or the cessation of an electrical impulse, the elapsed time and/or remaining time of the workout session, etc.), information to indicate whether an electrical impulse is on or off, and similar information. In the example of FIG. 1, the time information 122 is presented via the GUI 100 as a digital timer to indicate the time remaining to a particular event (e.g., the time remaining in a current exercise movement of the workout session, which may inform the user regarding an amount of time remaining before a relaxation period when the user can take a break in between exercise movements).

Although the example of FIG. 1 depicts various graphical elements overlaid atop media content 102 at various locations on a display, the specific locations where the elements are displayed may vary. In general, it may be preferable to overlay graphical elements around a periphery of the display area (as opposed to the center of the display area) so as to avoid (as much as possible) occluding the media content 102, such as the instructor, who may be performing exercise movements at or near the center of the display area. On relatively small displays (e.g., mobile phones), it may be difficult to avoid occluding the media content 102 (e.g., the instructor) without making text and other graphical elements illegible. In some embodiments, the graphical elements/overlays may be rendered in a semi-transparent manner so as to help the user see the media content 102 behind the graphical elements.

In some embodiments, the graphical elements of the GUI 100 may be movable on the display, such as by touching and holding a finger on the display at a location of the graphical element and dragging the element to a different location in the GUI 100. For example, the user may touch and drag one or both of the selectable elements 106 to move the element(s) from the bottom of the display to the middle or the top of the display. If other graphical elements are presented at those locations in the GUI 100, those graphical elements may automatically relocate to a different location in the GUI 100. For example, if the user were to drag both of the selectable elements 106 to the top of the GUI 100, the names of the exercise movements 118, 120 and the time information 122 may automatically shift downward, towards the middle of the GUI 100. A user may also be able to customize which graphical elements are presented via the GUI 100, the size of those elements, the color scheme, style of text, language, etc., by setting one or more preferences in user settings. For example, the user may set a preference for the selectable elements 106 to be omitted from the GUI 100 by default, but the selectable elements 106 may be presented via the GUI 100 whenever the user provides a particular type of user input (e.g., whenever the user touches the touchscreen at any location). It is also to be appreciated that the specific sizes, styles, and forms of the graphical elements shown in the GUI 100 of FIG. 1 are nonlimiting to the present disclosure and are merely exemplary, as other sizes, styles, and forms of graphical elements may be implemented.

Figure 2:
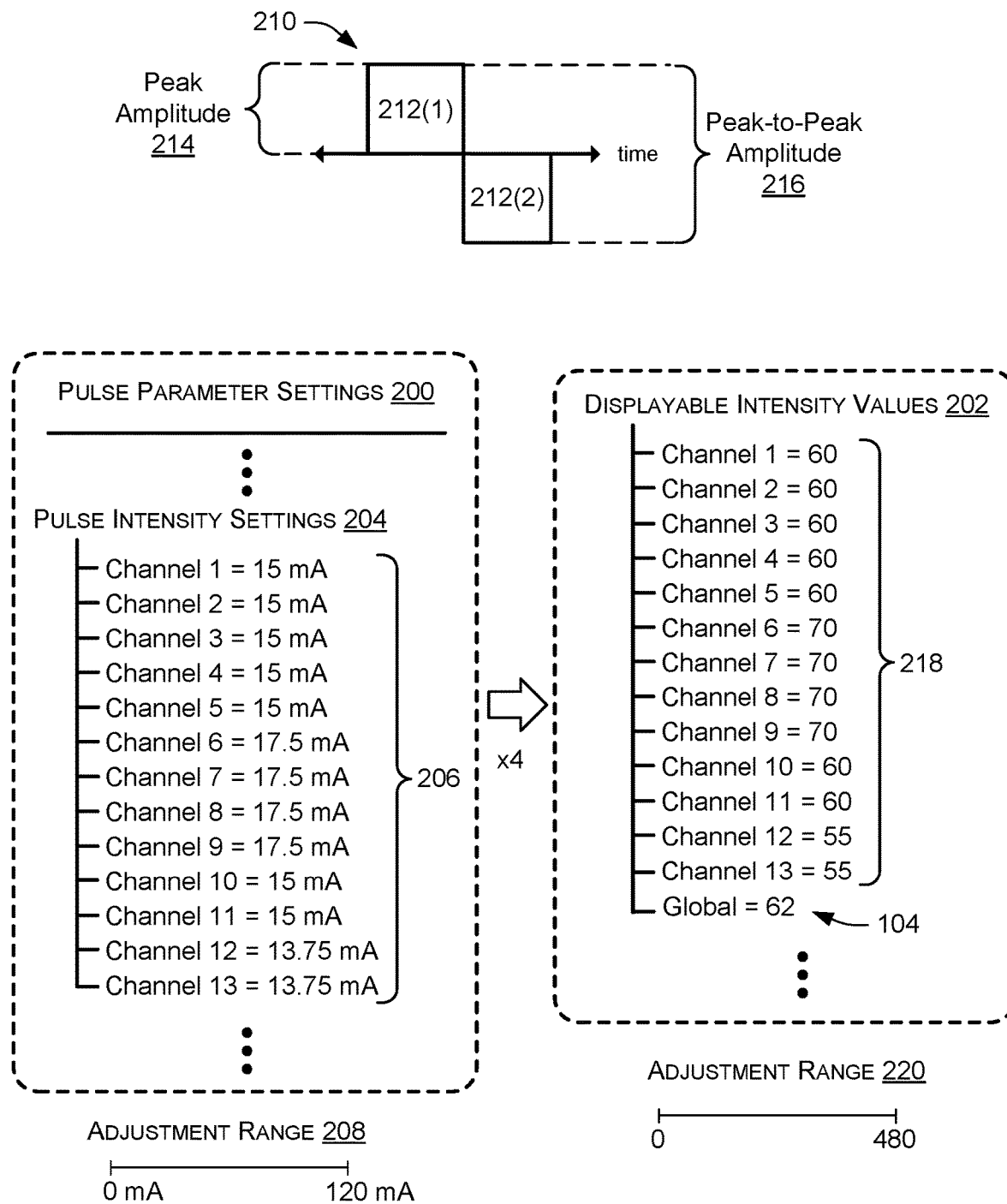
FIG. 2 is a schematic diagram showing example pulse parameter settings for delivery of electrical impulses via pairs of electrodes of an EMS suit, as well as displayable intensity values that are derived from pulse intensity settings.

FIG. 2 is a schematic diagram showing example pulse parameter settings 200 for delivery of electrical impulses via pairs of electrodes of an EMS suit, as well as displayable intensity values 202 that are derived from pulse intensity settings 204. To illustrate, when a user is wearing an EMS suit, as described in more detail below, electrical impulses delivered via electrodes elicit muscle contraction of the muscle groups that are disposed underneath the electrodes. Individual pairs of electrodes may correspond to individual channels that are usable for delivery of electrical impulses, one channel after another. Accordingly, one or more processors may cause circuitry of the EMS suit to deliver electrical impulses to individual channels of multiple channels sequentially (or in the sequence), one channel after another, and in accordance with the pulse parameter settings 200. FIG. 2 shows that the pulse parameter settings 200 may include, without limitation, pulse intensity settings 204. The pulse parameter settings 200, including the pulse intensity settings 204, may be stored in memory of a system including the EMS suit so that the pulse parameter settings 200 can be referenced during operation of the EMS suit (e.g., during the processing of a series of frames to deliver electrical impulses via electrodes of the EMS suit).

FIG. 2 shows how the pulse intensity settings 204 can be set to values 206. These values 206 may vary across the available channels, and the values 206 are sometimes referred to herein as "channel intensity values 206" because each value 206 is specific to a particular channel of multiple channels. FIG. 2 shows an example of a 13-channel EMS suit, and where the values 206 for each channel can, but do not have to, vary channel-by-channel. This means that each channel can be set to a value 206 for that channel, independently of the other channels. Although a 13-channel EMS suit is depicted in FIG. 2, any number of channels can be implemented.

An adjustment range 208 is also depicted in FIG. 2. The channel intensity values 206 may be adjustable over this adjustment range 208, which ranges from a minimum intensity value (e.g., zero) to a maximum intensity value (e.g., 120 mA). The channel intensity values 206 may be adjustable in any suitable increment over the adjustment range 208, such as increments that correspond to a fraction of a milliamp (mA). In some embodiments, the channel intensity values 206 are adjustable over the adjustment range 208 in increments of a quarter of a milliamp (or 0.25 mA increments) based on an adjustment of a corresponding displayable channel intensity value 218 by one. For example, any given channel intensity value 206 may be increased from 15 mA to 15.25 mA, and subsequently increased from 15.25 mA to 15.5 mA, and so on and so forth, and these individual adjustments of 0.25 mA may occur in response to a user adjusting a corresponding displayable channel intensity value 218 by one. Decreasing the channel intensity value 206 may occur in a similar fashion (e.g., in 0.25 mA decrements).

FIG. 2 also shows an example type of pulse 210 called a "biphasic pulse", which may be used to elicit muscle contraction of a user wearing the EMS suit disclosed herein. The biphasic pulse 210 is shown in part to illustrate what is meant herein by the term "pulse intensity". For a biphasic pulse 210 (i.e., a pulse having two phases 212; one positive phase 212(1) and one negative phase 212(2)), the "pulse intensity" can mean the peak amplitude 214 of the electrical pulse 210, the "peak" amplitude 214 meaning the peak (maximum) amplitude measured from zero for a given phase 212 of the pulse 210, or, in the alternative, the "pulse intensity" can mean the peak-to-peak amplitude 216 of the pulse 210, the "peak-to-peak" amplitude meaning the amplitude measured from the peak (maximum) of one (e.g., positive) phase 212(1) to the peak (maximum) of the next (e.g., negative) phase 212(2). It is to be appreciated that a peak-to-peak amplitude 216 is not applicable to a monophasic pulse, since a monophasic pulse includes only a single phase that is either positive or negative. The pulse intensity may be expressed using any suitable unit of measurement. In a current-controlled system for example, the pulse intensity may be expressed as a number of milliamps (mA), or any other suitable unit of measurement for electrical current. This is shown in the example of FIG. 2 where the channel intensity values 206 are expressed as numbers of milliamps (mA). However, in a voltage-controlled system for instance, the pulse intensity may be expressed as a number of volts (V), or any other suitable unit of measurement of electrical voltage. In the example of FIG. 2, the channel intensity values 206 may represent the peak amplitudes 214 of the respective electrical pulses 210 delivered on each channel, such as a peak amplitude 214 of 15 mA via Channel 1, a peak amplitude 214 of 15 mA via Channel 2, a peak amplitude of 15 mA via Channel 3, and so on and so forth, as depicted in FIG. 2, by way of example and not limitation.

It is to be appreciated that any suitable current types can be used to deliver electrical impulses via the electrodes of an EMS suit disclosed herein, including, without limitation, alternating current (AC) and pulsatile (or pulsed) current. Moreover, any suitable waveforms can be used to deliver the electrical impulses via the electrodes of the EMS suit, including, without limitation, waveforms of a monophasic shape, biphasic shape, or polyphasic shape, which may be symmetrical or asymmetrical, and balanced or unbalanced. In some embodiments, electrical impulses are delivered using waveforms that are symmetrical, balanced, and biphasic, as shown in FIG. 2. During a given pulse of electrical energy delivered via a pair of electrodes, current may flow between a pair of electrodes by traveling through a portion of the user's body (e.g., the muscle tissue underlying the pair of electrodes).

Although FIG. 2 depicts pulse intensity settings 204 and not any other pulse parameter settings 200, it is to be appreciated that the pulse parameter settings 200 may include other pulse-related settings (denoted by the ellipses in FIG. 2) including, without limitation, a frequency setting (e.g., the number of pulses per second, measured in Hertz (Hz)), an inter-pulse interval setting (e.g., the time between individual pulses, or an "OFF time"), a phase width setting (e.g., which may be used for asymmetrical waveforms in addition to pulse width settings), pulse width setting (e.g., elapsed time (duration) from the beginning of the first phase of a pulse to the end of the last phase of the pulse), an interphase interval setting (e.g., the time between phases of a pulse), a ramp up time setting (e.g., the time it takes for the current intensity to increase from zero to its maximum intensity), a plateau time setting (e.g., the time during which the pulse remains at a maximum intensity), and/or a ramp down time setting (e.g., the time it takes for the current intensity to decrease from its maximum intensity to zero). Although FIG. 2 depicts a maximum intensity of the adjustment range 208 as 120 mA, the maximum intensity (or current-cap) value to which the pulses (i.e., the channel intensity values 206) are adjustable may be about 90 mA, about 100 mA, about 110 mA, or about 120 mA. The maximum intensity (or current-cap) may be based on the hardware limitation of the EMS suit and/or the system in which the EMS suit is implemented, or the maximum intensity (or current-cap) may be implemented in software of the EMS suit and/or the system in which the EMS suit is implemented. If pulse width settings represent phase width, the pulse width settings may be set to values within a range of about 175 microseconds (µs) to about 400 µs. If biphasic pulses are delivered during operation of the EMS suit, and if pulse width settings represent pulse width, the pulse width settings may be set to values within a range of about 350 µs to about 800 µs. Frequency (or frame rate) may be set within a range of about 80 Hz to about 120 Hz. However, these are merely exemplary values, and other pulse parameter settings 200 may be utilized.

FIG. 2 further illustrates displayable intensity values 202, meaning values that may be displayed in lieu of displaying the channel intensity values 206 (e.g., values 206 expressed in milliamps (mA)). The displayable intensity values 202 may be formulated or derived from the channel intensity values 206 in the pulse intensity settings 204. For example, each channel intensity value 206 may be multiplied by a predefined number to generate displayable channel intensity values 218, which are sometimes referred to herein as "channel-specific intensity values 218", or channel-specific values 218" to differentiate from "channel subset intensity values" (described in more detail below). In the example of FIG. 2, this predefined number is the number "4". For example, with respect to Channel 1, the channel intensity value 206 of 15 mA may be multiplied by "4" to generate a corresponding displayable channel intensity value 218 of "60" for Channel 1. This operation can be carried out for the remaining channels to derive the displayable channel intensity values 218. A global intensity value 104 (which was introduced in FIG. 1) is also considered to be one of the displayable intensity values 202. If the global intensity value 104 is computed as the average of the displayable channel intensity values 218, the global intensity value 104 may be formulated as a value of "62" in the example of FIG. 2. This global intensity value 104 can be displayed via a GUI, such as the GUI 100 depicted in FIG. 1. In addition, other displayable intensity values 202 may be derived from subsets of displayable channel intensity values 218, sometimes referred to herein as "channel subset intensity values" or "channel subset values." For example, a channel subset intensity value associated with Channels 5 and 6 (which is a subset of channels) may be derived as the average of the displayable channel intensity values 218 for those channels, or (60+70)÷2=65.

Another adjustment range 220 is also depicted in FIG. 2. The displayable channel intensity values 218, the global intensity value 104, and or channel subset intensity values may be adjustable over the adjustment range 220, which ranges from a minimum intensity value (e.g., zero) to a maximum intensity value (e.g., 480). The displayable channel intensity values 218, the global intensity value 104, and/or channel subset intensity values may be adjustable in any suitable increment over the adjustment range 220, such as increments of one. For example, the displayable channel intensity value 218 for Channel 1 may be increased from "60" to "61", and subsequently increased from "61" to "62", and so on and so forth. Decreasing the displayable channel intensity values 218 may occur in a similar fashion (e.g., in decrements of a single integer). The global intensity value 104 and/or a channel subset intensity value may be similarly adjusted over the adjustment range 220. One reason that the displayable channel intensity values 218 are formulated as a multiple of the channel intensity values 206 is for ease of use when adjusting the intensity. That is, instead of displaying a number of milliamps of electrical current via the GUI 100 and having the user adjust the pulse intensity in increments of, say, 0.25 mA, it may be easier (from a usability standpoint) for the user to adjust the displayable intensity values 202 by single integer increments/decrements, seeing as how it is more intuitive for users to adjust levels in this manner. Furthermore, since the displayable channel intensity values 218 are formulated as a multiple of a corresponding channel intensity values 206, and since the global intensity value 104 and/or channel subset intensity values is/are derived from the displayable channel intensity values 218 (e.g., by computing the average of the values 218), the displayable intensity values 202 are also meaningful to users who are viewing the displayable intensity values 202. For example, if the displayable channel intensity value 218 for Channel 9 is set to "480", the user can readily appreciate that they are experiencing the maximum intensity of electrical impulses via Channel 9, and that they cannot increase the intensity any higher on Channel 9. Likewise, if the global intensity value 104 is set to "480", this means that all of the channels are set to intensity values 218 of "480", and the user can readily appreciate that this is truly the maximum intensity of electrical impulses that can be delivered via the electrodes of the EMS suit.

Figure 3:
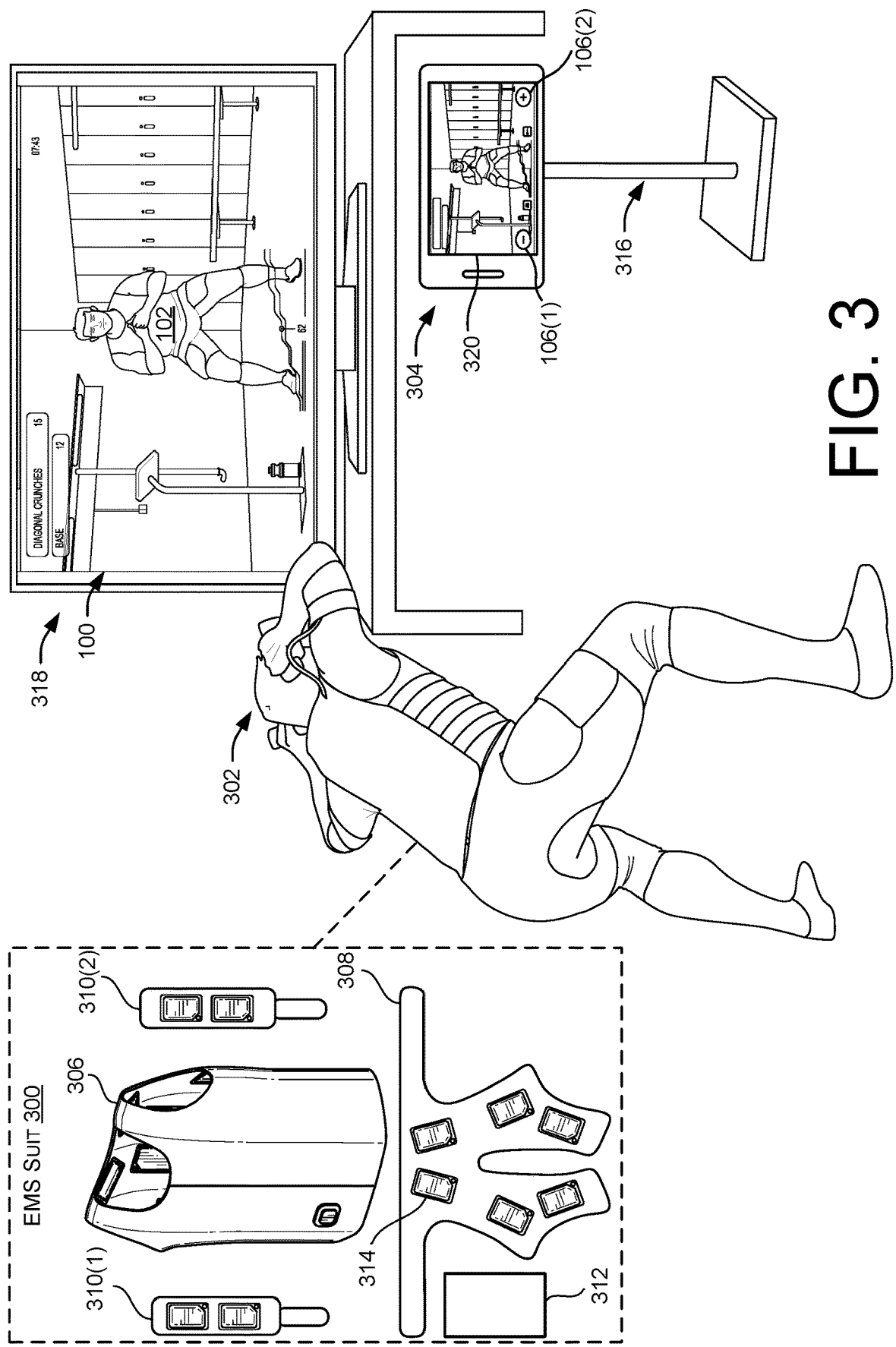
FIG. 3 illustrates a user who is using an EMS suit to exercise while following along with media content featuring an instructor conducting a workout session. The user can view one or more intensity values presented as a graphical overlay atop the media content, and may adjust the one or more intensity values by providing user input to a nearby computing device.

FIG. 3 illustrates a user 302 who is using an EMS suit 300 to exercise while following along with media content 102 featuring an instructor conducting a workout session. The user 302 can view one or more of the displayable intensity values 202 presented as a graphical overlay atop the media content 102, and may adjust the one or more intensity values 202 by providing user input to a nearby computing device 304, as will be illustrated in greater detail with reference to the following figures.

As shown in FIG. 3, the EMS suit 300 may comprise a vest portion 306, a pants portion 308 (sometimes referred to herein as a "shorts portion 308"), and/or at least two arm bands 310 including a right arm band 310(1) and a left arm band 310(2). The vest portion 306 is to be worn on an upper trunk of a user's body. The pants portion 308 is to be worn on a lower trunk and/or legs (e.g., upper legs) of the user's body. The arm bands 310 are to be worn on arms (e.g., upper arms) of the user's body. To secure the EMS suit 300 on a user's body, each portion 306/308/310 of the EMS suit 300 may include one or more straps, fasteners (e.g., hook-and-loop fasteners, zippers, buttons, clips, latches, etc.) to secure and/or tighten various parts of the EMS suit 300 to ensure a snug, yet comfortable, fit of the EMS suit 300 on the user's body.

FIG. 3 also shows the user 302 wearing the example EMS suit 300. An impulse pack 312, which may be part of the EMS suit 300, may house electronic components (e.g., a power source, such as batteries, processor(s)/controller(s), circuitry, etc.) for delivering electrical impulses via electrodes 314 of the EMS suit 300. The impulse pack 312 may couple to any one or more of the portions 306/308/310 of the EMS suit 300 via a wire(s)/connector and/or wirelessly. When the user 302 is wearing the EMS suit 300, electrical impulses delivered at suitable pulse parameters via the electrodes 314 elicit muscle contraction of the muscle groups that are disposed underneath the electrodes 314. Each electrode 314 may be connected (e.g., via wired means and/or wireless means) to electronics for delivering the electrical impulses (e.g., electronics of an impulse pack 312).

The EMS suit 300 may be programmed with the pulse parameter settings 200 as presets before the suit 300 is distributed to a merchant and/or an end user (e.g., a fitness center, individual consumer, etc.). The pulse parameter settings 200, as discussed with reference to FIG. 2, may relate to any suitable type of pulse parameters, such as pulse intensity settings 204 for the delivery of electrical impulses at a particular intensity. The manufacturer of the EMS suit 300 may additionally, or alternatively, set other pulse parameter presets, such as pulse width presets, frequency presets, and the like. The user 302 may adjust one or more of these presets (e.g., in a user settings menu of a client application), and, for at least the pulse intensity settings 204, the user 302 can adjust the pulse intensities on-the-fly, during operation of the EMS suit 300.

The user 302 in FIG. 3 is shown as wearing the EMS suit 300 while engaging in a workout session at the user's 302 home, but the user's 302 home is merely an exemplary environment in which the EMS suit 300 can be used. The user 302 may be in possession of a personal computing device 304, such as a tablet, a laptop, a mobile phone, etc. FIG. 3 depicts an example of a personal computing device 304 in the form of a tablet computer. The user 302 may place his/her computing device 304 on a stand 316 so that it is easily accessible to the user 302 during the workout session, and so that the user 302 does not have to hold the device 304 to provide user input thereto. The device 304 may be playing back media data corresponding to the media content 102 that is featuring an instructor conducting a workout session. In the example of FIG. 3, the device 304 is casting the media content 102 to a peripheral system 318, which may include speakers to output audio content, as well as a display to output image content. In this example, the peripheral system 318 is a living room television in the user's 302 living room. It is to be appreciated that the media content 102 may comprise video content and audio content, and that the video content may be output on a first output device (e.g., the display of the peripheral system 318) while the audio content is being output via a second output device (e.g., a speaker(s) of the device 304, or a separate speaker, etc.), or vice versa.

The EMS suit 300 may be communicatively coupled to the computing device 304 (e.g., wirelessly). The computing device 304 may store an executable application (e.g., code, computer-executable instructions, etc.) that is configured to, among other things, adjust pulse parameter settings 200 of the EMS suit 300. For example, an application may be downloaded to the computing device 304 from a remote system over a wide area network (e.g., the Internet) and executed on the computing device 304 to control various aspects of the EMS suit 300. For example, the device 304, via the downloaded application, may process command data to transmit commands to the EMS suit 300 at appropriate times so that the user 302 feels electrical impulses at the proper times (e.g., when the instructor featured in the media content 102 issues a verbal command to begin an exercise movement and/or begins demonstrating the exercise movement, the user 302 may feel a muscle contraction elicited by the delivery of electrical impulses via the electrodes 314 of the EMS suit 300). The command data, when processed by the device 304, may also cause commands to be transmitted from the device 304 to the EMS suit 300 for adjusting the global intensity value 104 during the workout session based at least in part on a pre-programmed sequence of global intensity values.

FIG. 3 depicts an example where the application executing on the computing device 304 may also cause display of the GUI 100 introduced in FIG. 1. The GUI 100 may be displayed on a display 320 of the computing device 304 and/or on a display of the peripheral system 318, such as by casting the GUI 100 from the device 304 to the peripheral system 318 in FIG. 3. As described with reference to FIG. 1, the GUI 100 allows for adjusting particular pulse parameter settings 200 of the EMS suit 300, such as pulse intensities. For example, the user 302 may adjust the global intensity value 104 (and/or the user 302 may adjust a channel subset intensity value, or a channel-specific intensity value(s) 218) by selecting a selectable element 106 presented on the GUI 100, or by issuing other types of user input (e.g., voice commands, gestures, etc.). Further details regarding how the user 302 may adjust pulse intensity settings 204 will be described in more detail with reference to the following figures.

FIG. 4A is an example of a GUI 400A that may be presented on a display, and a flow diagram of an example process 402 for presenting the GUI 400A. The example GUI 400A of FIG. 4A may be presented after user selection of the global intensity stabilizer element 108, which is also presented in the example GUI 100 shown in FIG. 1. The example GUI 400A of FIG. 4A illustrates how the user 302 may fix the global intensity value 104 for a remainder of a workout session using the global intensity stabilizer element 108. For example, the user 302 may want to prevent the global intensity value 104 from automatically increasing any further above a current value for the remainder of the workout session, and the user 302 may do so by selecting the element 108.

The processes described herein are illustrated as a collection of blocks in a logical flow graph, which represent a sequence of operations that can be implemented in hardware, software, or a combination thereof. In the context of software, the blocks represent computer-executable instructions that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the processes.

With reference to the example process 402 shown in FIG. 4A, at 404, a global intensity stabilizer element 108 may be presented on a display, such as via the GUI 100, in an unselected state. At 406, logic (e.g., a processor executing computer-executable instructions) may determine whether the global intensity stabilizer element 108 has been selected. If the element 108 has not been selected, the process 402 may follow the "NO" route from block 406 to block 404 by continuing to present the element 108 for selection (e.g., in an unselected state). If, however, the logic determines that the global intensity stabilizer element 108 has been selected, the process 402 may follow the "YES" route from block 406 to block 408.

At 408, the logic may override a pre-programmed sequence of global intensity values with instructions to fix the global intensity value 104 at a current value for a remainder of the workout session. At 410, a modified pre-programmed sequence of global intensity values may be presented on the display. This is shown in FIG. 4A by the curve 412(1), which depicts global intensity values plotted over time, where the curve 412(1) is flat after the element 114 to indicate that the global intensity value 104 will remain fixed at the current value for the remainder of the workout session.

FIG. 4A shows a state of the GUI 400A after selection of the global intensity stabilizer element 108. In response to selection of the element 108, the graph 110 changes by converting the first curve 112(1)—which, prior to selection of the element 108, plotted a pre-programmed sequence of increasing global intensity values in front of (e.g., to the right of) the element 114—into a modified first curve 412(1) shown in FIG. 4A. The modified first curve 412(1) depicts a flat line in front of (e.g., to the right of) the element 114 to indicate that the global intensity value 104 will remain fixed at its current value for a remainder of the workout session. The GUI 400A may also transition the global intensity stabilizer element 108 to a selected state by using a visual indicator (e.g., highlighting the element 108, changing the color of the element 108, etc.). By selecting the element 108 again, the user 302 may toggle back to the original workout session where the original pre-programmed sequence of increasing global intensity values are shown on the first curve 112(1) of FIG. 1. In this case, the GUI 400A may revert back to the GUI 100 by changing the graph 110 to include the first curve 112(1) and the second curve 112(2), as depicted in FIG. 1.

FIG. 4B is another example of a GUI 400B that may be presented on a display, and a flow diagram of an example process 414 for presenting the GUI 400B. The example GUI 400B of FIG. 4B may be presented after user selection of the channel intensity adjustment element 116, which is also presented in the example GUI 100 shown in FIG. 1, and after selection of a suit portion element 416(2) (e.g., a "vest" icon 416(2)) that may be presented after the user selection of the channel intensity adjustment element 116. The example GUI 400B of FIG. 4B illustrates how a user 302 can adjust an intensity value 430 associated with the vest portion 306 of the EMS suit 300.

With reference to the example process 414 shown in FIG. 4B, at 418, a channel intensity adjustment element 116 may be presented on a display, such as via the GUI 100, in an unselected state. At 420, logic (e.g., a processor executing computer-executable instructions) may determine whether the channel intensity adjustment element 116 has been selected. If the element 116 has not been selected, the process 414 may follow the "NO" route from block 420 to block 418 by continuing to present the element 116 for selection (e.g., in an unselected state). If, however, the logic determines that the channel intensity adjustment element 116 has been selected, the process 414 may follow the "YES" route from block 420 to block 422.

FIG. 4B shows a state of the GUI 400B after selection of the channel intensity adjustment element 116. In response to selection of the element 116, the global intensity value 104, the graph 110, and the global intensity stabilizer element 108 are removed from the display, and, at block 422, a set (or array) of channel identifier elements 424 and multiple suit portion elements 416 (e.g., a "pants" or "shorts" icon 416(1) and a "vest" icon 416(2)) are presented on the display, as shown in the GUI 400B of FIG. 4B. Individual ones of the channel identifier elements 424 are selectable and they identify the multiple channels of the EMS suit 300. The multiple suit portion elements 416, including, for example, a "pants" icon 416(1) and a "vest" icon 416(2), are also selectable and they identify multiple portions of the EMS suit 300, such as the pants portion 308 and the vest portion 306 depicted in FIG. 3. FIG. 4B shows a state of the GUI 400B after selection of the channel intensity adjustment element 116. In response to selection of the element 116, the channel identifier elements 424 are presented on the display, via the GUI 400B. In the example of FIG. 4B, the channel identifier elements 424 are presented as names of the muscle groups associated with the channels of the EMS suit 300. For example, a first channel identifier element 424(1) is presented as the name "Quads", a second channel identifier element 424(2) is presented as the name "Hamstrings", a third channel identifier element 424(3) is presented as the name "Glutes", a fourth channel identifier element 424(4) is presented as the name "Abs", a fifth channel identifier element 424(5) is presented as the name "Lower Back", a sixth channel identifier element 424(6) is presented as the name "Middle Back", a seventh channel identifier element 424(7) is presented as the name "Upper Back", an eight channel identifier element 424(8) is presented as the name "Chest", and a ninth channel identifier element 424(9) is presented as the name "Arms." These channel identifier element 424 (e.g., names) may be intuitive for the user 302 to understand how to adjust the intensity of electrical impulses delivered via different pairs of electrodes 314 on the EMS suit 300. However, any suitable name or identifier can be used to present the channel identifier element 424.

Referring again to the process 414, at 426, logic (e.g., a processor executing computer-executable instructions) may determine whether the suit portion element 416(2) (or, vest icon 416(2)) has been selected. If the element 416(2) has not been selected, the process 414 may follow the "NO" route from block 426 to block 422 by continuing to present the element 416(2) for selection (e.g., in an unselected state). If, however, the logic determines that the suit portion element 416(2) has been selected, the process 414 may follow the "YES" route from block 426 to block 428. At 428, in response to selection of the suit portion element 416(2), a channel subset intensity value 430 associated with the vest portion 306 of the EMS suit 300 may be presented on the display, via the GUI 400B.

To illustrate, as shown in FIG. 4B, after the user 302 selects the vest icon 416(2), a subset of the channel identifier elements 424 associated with the vest portion 306 of the EMS suit 300 may be selected (e.g., highlighted, changed in color, etc.), and the channel subset intensity value 430 may be presented to indicate to the user 302 a current intensity value associated with the subset of channels identified by the subset of channel identifier elements 424(4)-(8). In this example, the subset of channel identifier elements 424(4)-(8) correspond to pairs of electrodes 314 covering the user's 302 abs, lower back, middle back, upper back, and chest. The channel subset intensity value 430 may be derived similarly to how the global intensity value 104 is derived for the complete set of channels. For example, the channel subset intensity value 430 shown in the GUI 400B may be calculated as an average of the displayable channel intensity values 218 associated with the subset of channel identifier elements 424(4)-(8). In a simple example, each channel identified by the subset of channel identifier elements 424 (4)-(8) may be set to a displayable channel intensity value 218 of "38", and the channel subset intensity value 430 is calculated as the average of these displayable channel intensity values 218, which, in this example, is a value of "38". The actual pulse intensity for one of the channels identified by the subset of channel identifier elements 424(4)-(8) may be derived by dividing the displayable channel intensity value 218 for that channel (e.g., "38") by a predefined number (e.g., 38÷4=9.5 mA).

Furthermore, when the vest icon 416(2) is selected, as shown in FIG. 4B, the user 302 may adjust the channel subset intensity value 430 associated with the vest portion 306 of the EMS suit 300. For example, the user 302 may select the first intensity adjustment control 106(1) to decrease (e.g., decrement) the channel subset intensity value 430 (e.g., from "38" to "37"), or the user 302 may select the second intensity adjustment control 106(2) to increase (e.g., increment) the channel subset intensity value 430 (e.g., from "38" to "39"). In response to such an adjustment, the adjusted channel subset intensity value 430 may be presented via the GUI 400B and the corresponding adjustments may be made to the channel intensity values 206 associated with the subset of channel identifier elements 424(4)-(8) within the pulse intensity settings 204. The user 302 can select the channel intensity adjustment element 116 again to revert to a previous GUI, such as the GUI 100 shown in FIG. 1. In this way, the user 302 can navigate via the interactive GUI to adjust the intensity of electrical impulses delivered via a subset of channels instead of, or in addition to, adjusting the global intensity value 104. This is beneficial if the user 302 would like to adjust the intensity of the output exclusively on the vest portion 306 of the EMS suit 300, without adjusting the intensity of the output on the other portions (e.g., the pants portion 308 and the arm bands 310).

FIG. 4C is another example of a GUI 400C that may be presented on a display, and a flow diagram of an example process 432 for presenting the GUI 400C. The example GUI 400C of FIG. 4C may be presented after user selection of the channel intensity adjustment element 116, which is also presented in the example GUI 100 shown in FIG. 1, and after selection of a suit portion element 416(1) (e.g., a "pants" icon 416(1)) that is presented after the user selection of the channel intensity adjustment element 116. The example GUI 400C of FIG. 4C illustrates how a user 302 can adjust an intensity value 444 associated with the pants portion 308 of the EMS suit 300.

With reference to the example process 432 shown in FIG. 4C, at 434, a channel intensity adjustment element 116 may be presented on a display, such as via the GUI 100, in an unselected state. At 436, logic (e.g., a processor executing computer-executable instructions) may determine whether the channel intensity adjustment element 116 has been selected. If the element 116 has not been selected, the process 432 may follow the "NO" route from block 436 to block 434 by continuing to present the element 116 for selection (e.g., in an unselected state). If, however, the logic determines that the channel intensity adjustment element 116 has been selected, the process 432 may follow the "YES" route from block 436 to block 438.

FIG. 4C shows a state of the GUI 400C after selection of the channel intensity adjustment element 116. In response to selection of the element 116, the global intensity value 104, the graph 110, and the global intensity stabilizer element 108 are removed from the display, and, at block 438, a set (or array) of channel identifier elements 424 and multiple suit portion elements 416 (e.g., a "pants" icon 416(1) and a "vest" icon 416(2)) are presented on the display, via the GUI 400C. FIG. 4C shows a state of the GUI 400C after selection of the channel intensity adjustment element 116, after which the channel identifier elements 424 are presented on the display.

Referring again to the process 432, at 440, logic (e.g., a processor executing computer-executable instructions) may determine whether the suit portion element 416(1) (or, pants icon 416(1)) has been selected. If the element 416(1) has not been selected, the process 432 may follow the "NO" route from block 440 to block 438 by continuing to present the element 416(1) for selection (e.g., in an unselected state). If, however, the logic determines that the suit portion element 416(1) has been selected, the process 432 may follow the "YES" route from block 440 to block 442. At 442, a channel subset intensity value 444 associated with the pants portion 308 of the EMS suit 300 may be presented on the display, via the GUI 400C.

To illustrate, as shown in FIG. 4C, after the user 302 selects the pants icon 416(1), a subset of the channel identifier elements 424 associated with the pants portion 308 of the EMS suit 300 may be selected (e.g., highlighted, changed in color, etc.), and the channel subset intensity value 444 may be presented to indicate to the user 302 a current intensity value associated with the subset of channels identified by the subset of channel identifier elements 424(1)-(3). In this example, the subset of channel identifier elements 424(1)-(3) correspond to pairs of electrodes 314 covering the user's 302 quads, hamstrings, and glutes. The channel subset intensity value 444 may be derived similarly to how the global intensity value 104 is derived for the complete set of channels. For example, the channel subset intensity value 444 may be calculated as an average of the displayable channel intensity values 218 associated with the subset of channel identifier elements 424(1)-(3). In a simple example, each channel identified by the subset of channel identifier elements 424(1)-(3) may be set to a displayable channel intensity value 218 of "38", and the channel subset intensity value 444 is calculated as the average of these displayable channel intensity values 218, which, in this example, is a value of "38". The actual pulse intensity for one of the channels identified by the subset of channel identifier elements 424(1)-(3) may be derived by dividing the displayable channel intensity value 218 for that channel (e.g., "38") by a predefined number (e.g., 38÷4=9.5 mA).

Furthermore, when the pants icon 416(1) is selected, as shown in FIG. 4C, the user 302 may adjust the channel subset intensity value 444 associated with the pants portion 308 of the EMS suit 300. For example, the user 302 may select the first intensity adjustment control 106(1) to decrease (e.g., decrement) the channel subset intensity value 444 (e.g., from "38" to "37"), or the user 302 may select the second intensity adjustment control 106(2) to increase (e.g., increment) the channel subset intensity value 444 (e.g., from "38" to "39"). In response to such an adjustment, the adjusted channel subset intensity value 444 may be presented via the GUI 400C and the corresponding adjustments may be made to the channel intensity values 206 associated with the subset of channel identifier elements 424(1)-(3) within the pulse intensity settings 204. The user 302 can select the channel intensity adjustment element 116 again to revert to a previous GUI, such as the GUI 100 shown in FIG. 1. In this way, the user 302 can adjust the intensity of the output exclusively on the pants portion 308 of the EMS suit 300, without adjusting the intensity of the output on the other portions (e.g., the vest portion 306 and the arm bands 310). It is to be appreciated that other subsets of channels may be selectable in a similar manner, according to some embodiments, allowing for adjustment of any portion of the EMS suit 300 independently of other portions of the EMS suit 300. For example, a channel subset intensity value may correspond to channels associated with the right half of the EMS suit 300, channels associated with the left half of the EMS suit 300, etc.

FIG. 4D is another example of a GUI 400D that may be presented on a display, and a flow diagram of an example process 446 for presenting the GUI 400D. The example GUI 400D of FIG. 4D may be presented after user selection of the channel intensity adjustment element 116, which is also presented in the example GUI 100 shown in FIG. 1, and after selection of a channel identifier element 424. The example GUI 400D of FIG. 4D illustrates how a user 302 can adjust an intensity value associated with an individual channel, such as an intensity value 218(1) associated with the channel identifier element 424(1), which, in turn, corresponds to an individual channel of the EMS suit 300.

With reference to the example process 446 shown in FIG. 4D, at 448, a channel intensity adjustment element 116 may be presented on a display, such as via the GUI 100, in an unselected state. At 450, logic (e.g., a processor executing computer-executable instructions) may determine whether the channel intensity adjustment element 116 has been selected. If the element 116 has not been selected, the process 446 may follow the "NO" route from block 450 to block 448 by continuing to present the element 116 for selection (e.g., in an unselected state). If, however, the logic determines that the channel intensity adjustment element 116 has been selected, the process 446 may follow the "YES" route from block 450 to block 452.

FIG. 4D shows a state of the GUI 400D after selection of the channel intensity adjustment element 116. In response to selection of the element 116, the global intensity value 104, the graph 110, and the global intensity stabilizer element 108 are removed from the display, and, at block 452, a set (or array) of channel identifier elements 424 are presented on the display, via the GUI 400D. FIG. 4D shows a state of the GUI 400D after selection of the channel intensity adjustment element 116, after which the channel identifier elements 424 are presented on the display.

Referring again to the process 446, at 454, logic (e.g., a processor executing computer-executable instructions) may determine whether a channel identifier element 424 has been selected. If an element 424 has not been selected, the process 446 may follow the "NO" route from block 454 to block 452 by continuing to present the elements 424 for selection (e.g., in an unselected state). If, however, the logic determines that a channel identifier element 424 (e.g., the "Quads" icon 424(1)) has been selected, the process 446 may follow the "YES" route from block 454 to block 456. At 456, a channel-specific intensity value 218(1) associated with the "Quads" channel of the EMS suit 300 may be presented on the display, via the GUI 400D.

To illustrate, as shown in FIG. 4D, after the user 302 selects the channel identifier element 424(1) (e.g., the "Quads" icon 424(1)), the visual appearance of the selected element 424(1) may be changed (e.g., highlighted, changed in color, etc.), and the channel-specific intensity value 218(1) may be presented to indicate to the user 302 a current intensity value associated with the channel identified by the selected channel identifier elements 424(1). In this example, the channel identifier element 424(1) corresponds to a pair of electrodes 314 covering the user's 302 quads. The intensity value 218(1) associated with this selected element 424(1) is shown as a value of "27". The actual pulse intensity for the channel identified by the channel identifier element 424(1) may be derived by dividing the channel-specific intensity value 218(1) (e.g., "27") by a predefined number (e.g., 27÷4=6.75 mA).

Furthermore, when the channel identifier element 424(1) is selected, as shown in FIG. 4D, the user 302 may adjust the channel-specific intensity value 218(1) associated with the electrodes 314 of the EMS suit 300 covering the user's 302 quads. For example, the user 302 may select the first intensity adjustment control 106(1) to decrease (e.g., decrement) the channel-specific intensity value 218(1) (e.g., from "27" to "26"), or the user 302 may select the second intensity adjustment control 106(2) to increase (e.g., increment) the channel-specific intensity value 218(1) (e.g., from "27" to "28"). In response to such an adjustment, the adjusted channel-specific intensity value 218(1) may be presented via the GUI 400D and the corresponding adjustments may be made to the channel intensity value 206 associated with the channel identifier element 424(1) within the pulse intensity settings 204. The user 302 can select the channel intensity adjustment element 116 again to revert to a previous GUI, such as the GUI 100 shown in FIG. 1. In this way, the user 302 can adjust the intensity of the output exclusively on an individual channel of the EMS suit 300, without adjusting the intensity of the output on the other channels.

Figure 4E:
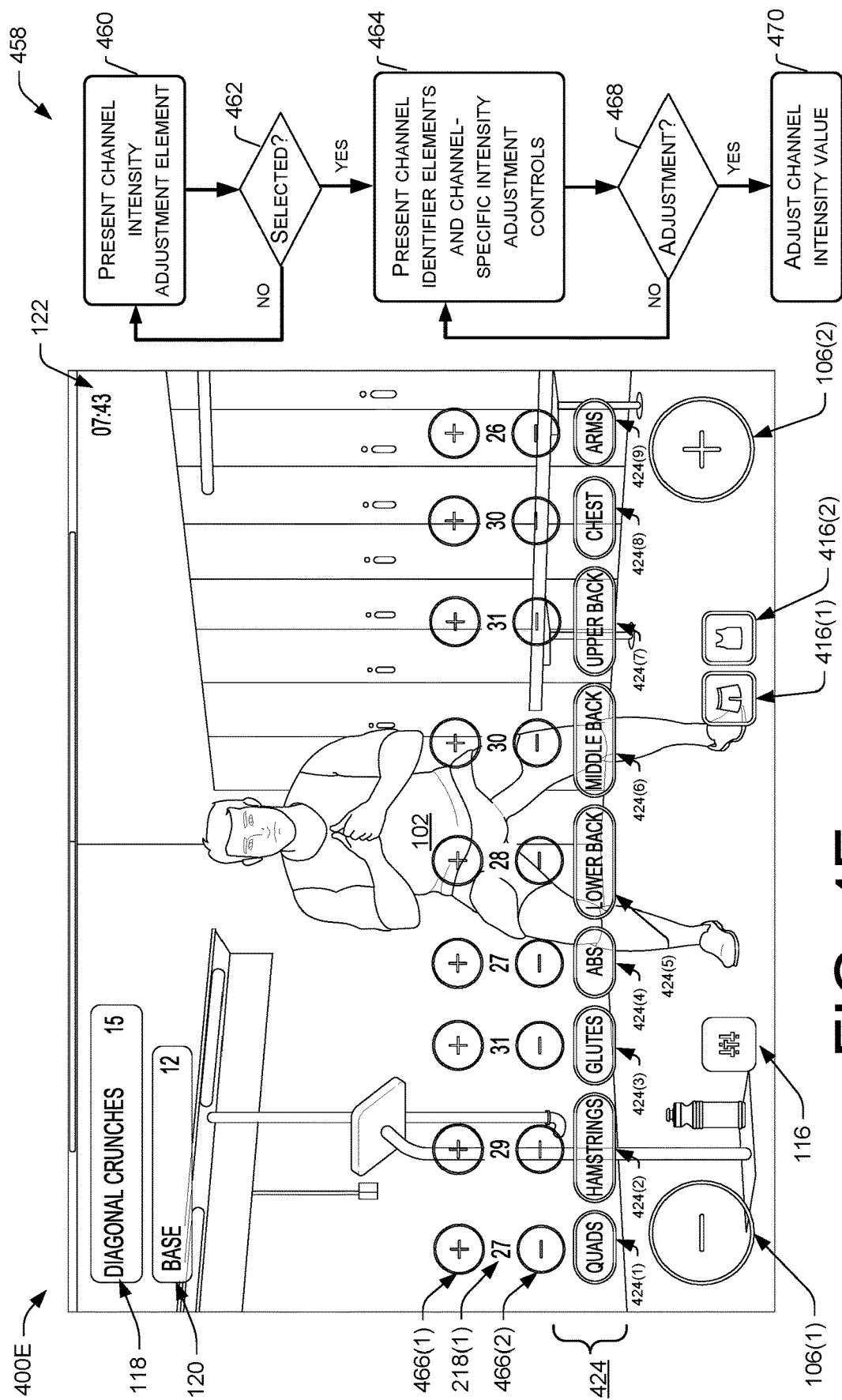
FIG. 4E is another example of a GUI that may be presented on a display, and a flow diagram of an example process for presenting the GUI. The example GUI of FIG. 4E may be presented after user selection of a selectable element presented in the example GUI shown in FIG. 1. The example GUI of FIG. 4E illustrates how a user can adjust an intensity value associated with an individual channel of the EMS suit, according to another embodiment.

FIG. 4E is another example of a GUI 400E that may be presented on a display, and a flow diagram of an example process 458 for presenting the GUI 400E. The example GUI 400E of FIG. 4E may be presented after user selection of the channel intensity adjustment element 116, which is also presented in the example GUI 100 shown in FIG. 1. The example GUI 400E of FIG. 4E illustrates how a user 302 can adjust an intensity value associated with an individual channel, such as an intensity value 218(1) associated with the channel identifier element 424(1), which, in turn, corresponds to an individual channel of the EMS suit 300.

With reference to the example process 458 shown in FIG. 4E, at 460, a channel intensity adjustment element 116 may be presented on a display, such as via the GUI 100, in an unselected state. At 462, logic (e.g., a processor executing computer-executable instructions) may determine whether the channel intensity adjustment element 116 has been selected. If the element 116 has not been selected, the process 458 may follow the "NO" route from block 462 to block 460 by continuing to present the element 116 for selection (e.g., in an unselected state). If, however, the logic determines that the channel intensity adjustment element 116 has been selected, the process 458 may follow the "YES" route from block 462 to block 464.

FIG. 4E shows a state of the GUI 400E after selection of the channel intensity adjustment element 116. In response to selection of the element 116, the global intensity value 104, the graph 110, and the global intensity stabilizer element 108 are removed from the display, and, at block 464, a set (or array) of channel identifier elements 424 are presented on the display, via the GUI 400E, and channel-specific intensity adjustment controls 466 are also presented proximate to (e.g., above) each channel identifier element 424 in the GUI 400E. For example, above the channel identifier element 424(1) for the "QUADS" channel, the GUI 400E presents a first channel-specific intensity adjustment control 466(1) (e.g., a "plus" icon) and a second channel-specific intensity adjustment control 466(2) (e.g., a "minus" icon). The example GUI 400E also presents the current channel-specific intensity value 218(1) to which the "QUADS" channel is set. In the state of the GUI 400E shown in FIG. 4E, these channel-specific intensity adjustment controls 466 may be utilized to adjust (e.g., increase or decrease) the channel-specific intensity values 218 independently. For example, the first channel-specific intensity adjustment control 466 (1), upon selection, may increase the channel-specific intensity value 218(1) from a current value (e.g., "27" in FIG. 4E) to an increased value (e.g., "28"), and the second channel-specific intensity adjustment control 466(2), upon selection, may decrease the channel-specific intensity value 218(1) from a current value (e.g., "27" in FIG. 4E) to a decreased value (e.g., "26"). In some embodiments, an individual selection (e.g., touch) of the first channel-specific intensity adjustment control 466(1) may increment the channel-specific intensity value 218(1) by one (e.g., from "27" to "28"), and an individual selection (e.g., touch) of the second channel-specific intensity adjustment control 466(2) may decrement the channel-specific intensity value 218(1) by one (e.g., from "27" to "26"). However, the system may adjust the channel-specific intensity values 218 by more than one with each selection of a channel-specific intensity adjustment control 466, in some embodiments. In some embodiments, a "touch-and-hold" type of user input detected on either of the channel-specific intensity adjustment controls 466 may cause the channel-specific intensity value 218 to continue adjusting until the user ceases touching the channel-specific intensity adjustment control 466, and the rate at which the adjustment occurs may gradually increase the longer the user holds the touch-based input on the channel-specific intensity adjustment control 466.

At block 468 of the process 458, if the user does not select one of the channel-specific intensity adjustment controls 466, the process 458 may follow the "NO" route from block 468 back to block 464 where the elements 424, 466, and 218 may continue to be presented. If, at block 468, the user selects one of the channel-specific intensity adjustment controls 466 to adjust the channel-specific intensity value 218(1), the process 458 may follow the "YES" route from block 468 to block 470 where logic of the system may determine, based on the adjusted displayable intensity value 218(1) for the "QUADS" channel, an amount by which to adjust the channel intensity value 206 for that channel. For example, if the "QUADS" channel is set to a channel intensity value of 6.75 mA, an adjustment of the displayable intensity value 218(1) from "27" to "28" may cause adjustment of the channel intensity value 206 in the pulse intensity settings 204 from 6.75 mA to 7 mA. After this adjustment, electrical impulses may be delivered at the new channel intensity values of 7 mA on the "QUADS" channel, and the adjusted displayable intensity value (e.g., "28") may be presented on a display proximate to (e.g., above) the channel identifier element 424(1) via the GUI 400E. The user 302 can select the channel intensity adjustment element 116 again to revert to a previous GUI, such as the GUI 100 shown in FIG. 1. In this way, the user 302 can adjust the intensity of the output exclusively on an individual channel of the EMS suit 300, without adjusting the intensity of the output on the other channels.

Figure 5:
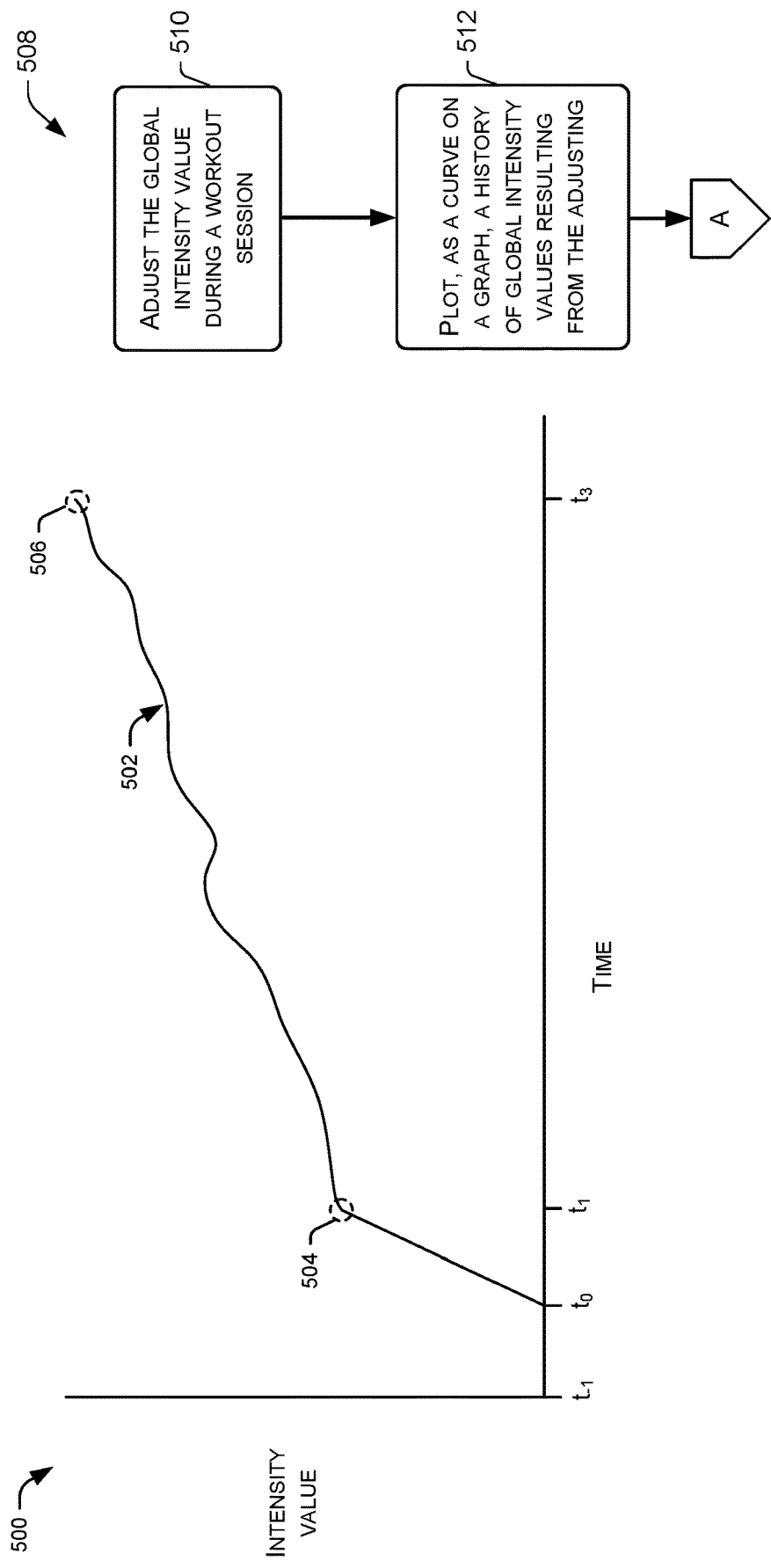
FIG. 5 illustrates a graph showing a history of intensity values plotted over time, and a flow diagram of an example process for generating the graph. The history of intensity values may be associated with a workout session.

FIG. 5 illustrates a graph 500 showing a history of intensity values 502 (e.g., global intensity values 104) plotted over time, and a flow diagram of an example process 508 for generating the graph 500. The history of intensity values 502 (sometimes referred to herein as an "intensity profile 502", or a "curve 502" of the graph 500) may be associated with a workout session. The curve 502 provides a visual aid to understand how the output of an EMS suit 300 may be controlled over a duration of the workout session. The graph 500 (or at least a portion thereof) may represent one of the curves 112 presented via the GUI 100 of FIG. 1 as a means of providing feedback to the user 302 while the user 302 is engaged in a workout session.

The time period from time, $t_{-1}$, to time, $t_0$, may represent a welcome segment of a workout session. During this welcome segment, media content 102 may be output on a display featuring an instructor who welcomes the user 302 to the workout session by providing introductory comments and information regarding the upcoming workout session, such as the exercise movements involved, targeted muscle groups, the type of fitness goals that is to be achieved, the duration of the workout session, etc. The time period from time, $t_0$, to time, $t_1$, may represent a start of an exercise portion where the EMS suit 300 starts to provide output in the form of electrical impulses delivered via electrodes 314 of the EMS suit 300. In some embodiments, this time period may represent a warm-up phase of the workout session (e.g., a two-minute warm up). During this time period, the output of the EMS suit 300 may ramp (e.g., linearly) from an intensity value of zero to a starting intensity value 504. For example, the starting intensity value 504 may be determined based on the intensity values that were output during a previous workout session specified in a user profile of the user 302. If there is no workout history on the user 302, the starting intensity value 504 may be based on a default intensity value, which may be based on information provided by the user 302 in advance, such as experience level, body type, fitness condition, etc.

The time period from time, $t_1$, to time, $t_3$, along the curve 502 may represent a period of time where the intensity of electrical impulses delivered via electrodes 314 of the EMS suit 300 progressively increases over the duration of the workout session to an ending intensity value 506 at the end of the exercise portion of the session. In some embodiments, this time period may represent a full body strength training (e.g., 15 minutes), followed by an abs and core training (e.g., 5 minutes), etc. For example, 150 seconds into the workout, the global intensity value 104 may increase by 1% overall during a full-body strength training portion, and so on and so forth. After time, $t_3$, the workout session (exhibited via media content 102) may include a goodbye segment where the instructor featured in the media content 102 is providing reminders and other tips for the user 302, as well as thanking the user 302 for participating in the workout session. In some embodiments, this may include, or be preceded by, a cool down phase of the workout session.

The history of intensity values 502 may therefore represent global intensity value 104 adjustments that include both a pre-programmed sequence of global intensity value 104 adjustments, as well as the manual adjustments made by the user 302 during the workout session, if any were made. In some embodiments, small breaks may be included throughout the workout session to allow for hydration or a change of position from standing to a ground-based set of exercises. This way, the user 302 can benefit from all the adjustments and instructions given as if the instructor featured in the media content 102 would operate his/her EMS suit 300.

Referring to the process 508, at 510, logic (e.g., a processor executing computer-executable instructions) may adjust the global intensity value 104 during the workout session, and at 512, the logic may plot, as a curve 502 on the graph 500, a history of global intensity values resulting from the adjusting. This curve 502, or a portion thereof, may be presented on a display (e.g., via a GUI) at any suitable time, such as before, during, and/or after a workout session. For example, the graph 500 (or at least a portion thereof) may represent one of the curves 112 presented via the GUI 100 of FIG. 1 as a means of providing feedback to the user 302 while the user 302 is engaged in a workout session. The history of intensity values 502 may be stored in memory of the system including the EMS suit 300, as described herein. For example, the history of intensity values 502 may be stored in local memory of the EMS suit 300, and/or local memory of the personal computing device 304, and/or the history of intensity values 502 may be uploaded over a wide area network (e.g., the Internet) to a remote computing system for maintaining the history of intensity values 502 in memory of the remote computing system and in association with a user profile of the user 302. At the start of each workout, when the user 302 launches a client application on the computing device 304, the history of intensity values 502 may be accessible (e.g., by the remote computing system, the computing device 304, etc.) for use in determining a starting intensity of the upcoming workout session, as described in more detail below.

In some embodiments, the curve 502 for a particular workout session may be associated with a particular modality of multiple modalities. For example, the multiple modalities may include, without limitation, a cardio modality, a strength training modality, a recovery modality, and the like. Each of these modalities may curate a unique intensity profile that is appropriate for the particular modality and may adjust the global intensity value 104 over the course of a workout session in accordance with the intensity profile for that modality. This allows for storing histories of intensity value adjustments (or curves 502) in association with a corresponding modality.

Over a series of workout sessions, one can appreciate that a large corpus of histories of global intensity values 502 may be aggregated and associated with times, days, weeks, months, years, etc., and associated with a given user profile of a user 302, and/or a given modality. In this way, the remote system and/or a client application of the user's 302 computing device 304 may analyze the histories of intensity values 502 aggregated for a given user 302 and/or across multiple users to generate interesting analysis results. This allows for tracking performance (at least in terms of intensity of electrical impulses delivered via an EMS suit 300) over time and determining various metrics associated with the histories. It is to be appreciated that, in addition to tracking adjustments to a global intensity value 104, adjustments to the channel intensity values of individual channels may be tracked as well, which allows for generating analytics at any level of granularity.

Figure 6:
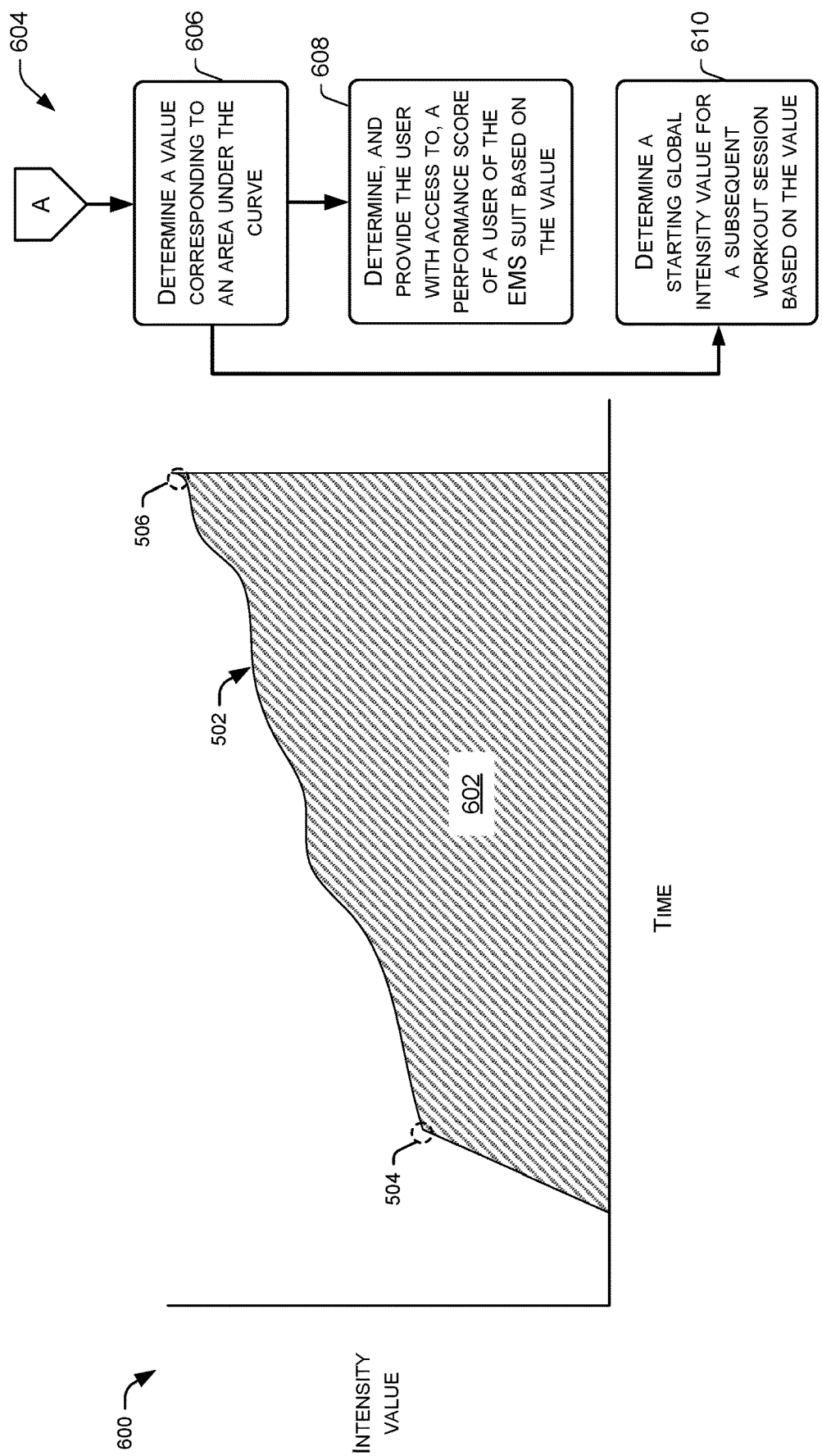
FIG. 6 illustrates a graph showing an area under a curve that represents accumulated output plotted over time.

FIG. 6 illustrates a graph 600 showing an area 602 under a curve 502 that represents accumulated output plotted over time. FIG. 6 also illustrates flow diagram of an example process 604 for determining a performance score and/or a starting intensity for a next workout session based on the area 602 under the curve 502.

As discussed with reference to FIG. 5, the history of intensity values 502 (or the curve 502) may represent global intensity value 104 adjustments that include a pre-programmed sequence of global intensity value 104 adjustments and/or manual adjustments made by the user 302 during the workout session. A value corresponding to the area 602 under the curve 502 may be indicative of the performance of a given user 302 associated with the curve 502, because the area 602 may represent the work performed to complete the workout session.

Referring to the process 604, at 606, logic (e.g., a processor executing computer-executable instructions) may determining a value corresponding to an area 602 under the curve 502. As indicated by the off-page reference "A" in FIGS. 5 and 6, the process 604 may continue from block 512 of the process 508 of FIG. 5, after the curve 502 is plotted as a history of global intensity values resulting from adjusting the global intensity value during a workout session. At 608, the logic may determine a performance score of a user 302 of the EMS suit 300 based at least in part on the value determined at block 606, and the user 302 may be provided with access to the performance score. For example, the performance score can be calculated and presented to the user 302 (e.g., via one of the GUIs described herein, via an email, a text, and/or a push notification sent to the user 302 and accessible via a computing device 304). This performance score may be provided to the user 302 at any suitable time, such as after completion of the workout session. In an illustrative example, a performance score determined at block 608 may comprise a "star rating" (e.g., 4 stars out of 5), a number of points (e.g., "you accrued 16,480 points today! Congratulations!"). Users 302 who receive such performance scores will quickly learn whether they are improving against themselves or not, and/or how they are competing against other users. This is enabled due to the way that global intensity values 104 are formulated from the pulse intensities of a multi-channel EMS suit 300, as described herein. That is, global intensity values 104 can be compared across multiple users and social aspects and related features can be enabled so that users can compete against each other, themselves, etc.

At 610, in addition to determining the performance score, or in the alternative, the logic may determine a starting global intensity value 104 for a subsequent workout session based at least in part on the value determined at block 606. In some embodiments, a rolling average of values corresponding to the area 602 under the curve 502 over the last "N" workout sessions may be calculated and used to determine the starting intensity of the next workout session. That way, if a user 302 has a bad day performance-wise, the "bad" performance won't impact the starting intensity as heavily as it would otherwise if a rolling average was not used. The system described herein may be configured to identify such anomalies (e.g., abnormally poor performances) and may down-weight the values corresponding to the area 602 under those curves 502 or ignore the those anomalous performances altogether for purposes of determining a starting intensity for an upcoming workout session.

At least one reason why the area 602 under the curve 502 may be used to determine a performance score and/or a starting intensity for a next workout session is because there is arguably an infinite number of different paths that can be taken from a starting intensity 504 to an ending intensity 506 over the course of a workout session. If, for example, a first user (User A) slowly and steadily increased the global intensity value 104 over the course of a workout session from the starting intensity 504 to the ending intensity 506, the area 602 under the curve 502 for User A may be very different from a second user (User B) who rapidly increased to an intensity that is close to the ending intensity 506 and thereafter increased the intensity by a relatively small amount over a larger portion of the workout session. In the former case, User A ramped up relatively slowly to the ending intensity 506, and, in the latter case, User B ramped up relatively quickly and stayed at a higher intensity for a larger percentage of the workout session's duration.

Figure 7:
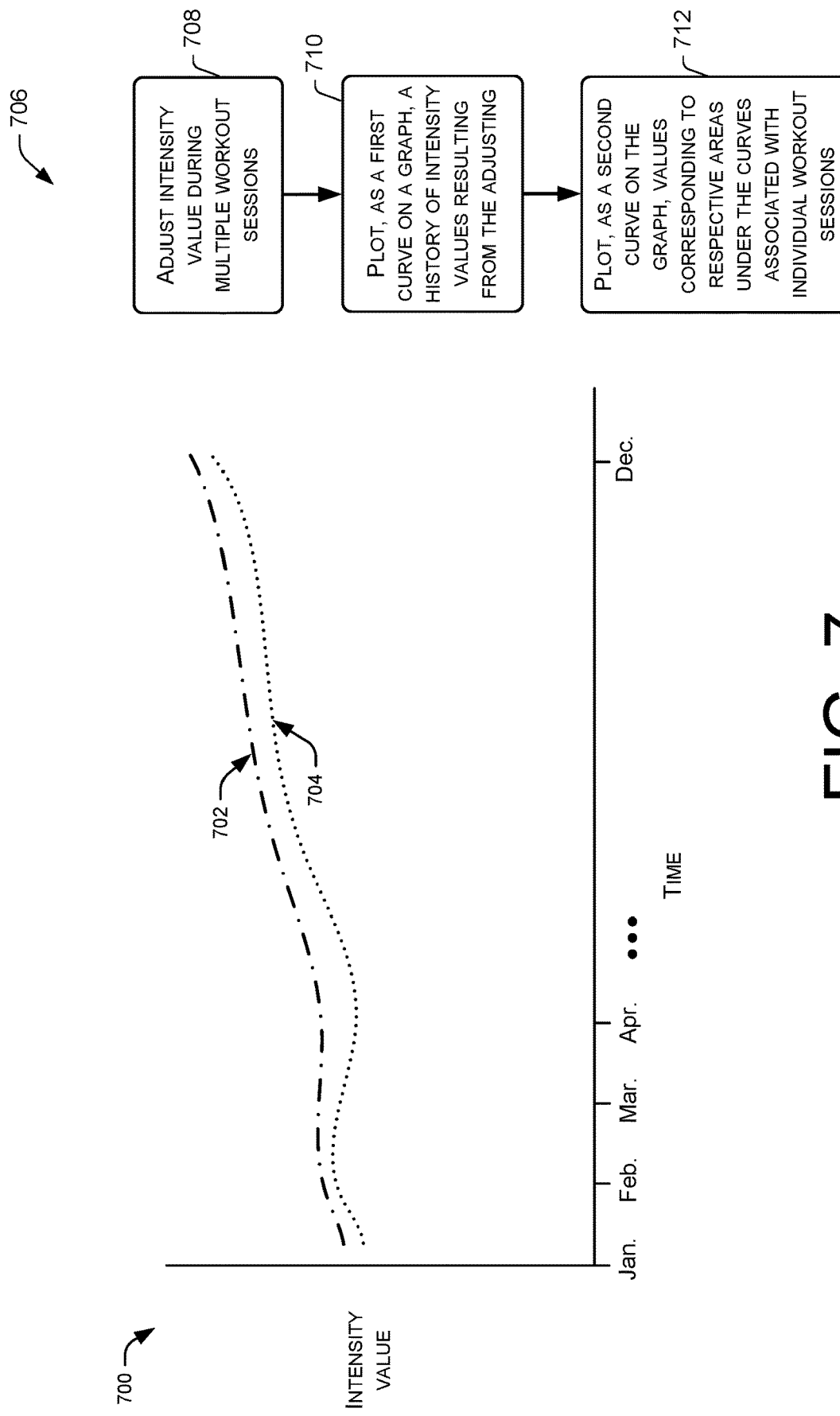
FIG. 7 illustrates a graph showing multi-session intensity profiles that may be plotted over any suitable time period that extends beyond a single workout session, and a flow diagram of an example process for generating the graph.

FIG. 7 illustrates a graph 700 showing multi-session intensity profiles that may be plotted over any suitable time period that extends beyond a single workout session, and a flow diagram of an example process 706 for generating the graph 700. For example, over time, as a user 302 performs multiple workout sessions where the intensity (e.g., global intensity 104) of electrical impulses delivered via an EMS suit 300 worn by the user 302 is tracked and saved for each workout session, these tracked intensity values over multiple histories of multiple workout sessions can be plotted over time to generate the curve 702. For example, the curve 702 may represent a history of intensity values that have been tracked for a give user 302 over the course of a period of time spanning several months, years, or the like. For example, a user 302 can view a history of intensity values plotted over the course of a year (e.g., 12 months) as the curve 702. Accordingly, the curve 702 may represent multiple curves 502 that are linked together in order to span multiple workout sessions.

Referring to the process 706, at 708, logic (e.g., a processor executing computer-executable instructions) may adjust an intensity value during multiple workout sessions for a given user 302 who is wearing and using an EMS suit 300 during the multiple workout sessions. At 710, the logic may plot, as a first curve 702 on a graph 700, a history of intensity values resulting from the adjusting at block 708. These intensity values that constitute the first curve 702 may be stored in memory. At 712, the logic may plot, as a second curve 704 on the graph 700, values corresponding to respective areas under the curves associated with individual workout sessions of the multiple workout sessions. The curves 702/704 may be presented on a display (e.g., via a GUI) at any suitable time, such as before, during, or after a workout session. As described with reference to FIG. 6, an area 602 under a curve 502 for an individual workout session may be determined, and, since the curve 702 in the graph 700 may represent multiple curves 502 that are linked together, multiple values that represent the respective areas under those curves 502 can be determined, and the values may be plotted as the second curve 704. These values that constitute the second curve 704 may also be stored in memory. Alternatively, the curve 704 may represent performance scores plotted over time. In any case, user-specific workout performance can be evaluated on any timescale by tracking histories of global intensity value 104 adjustments and/or by tracking adjustments to channel intensity values 206 that were made over the course of multiple workout sessions. Additionally, or alternatively, the graph 700 may show a comparison of workout performances associated with two or more users, such as friends, a peer group, social contacts, etc.

Figure 8:
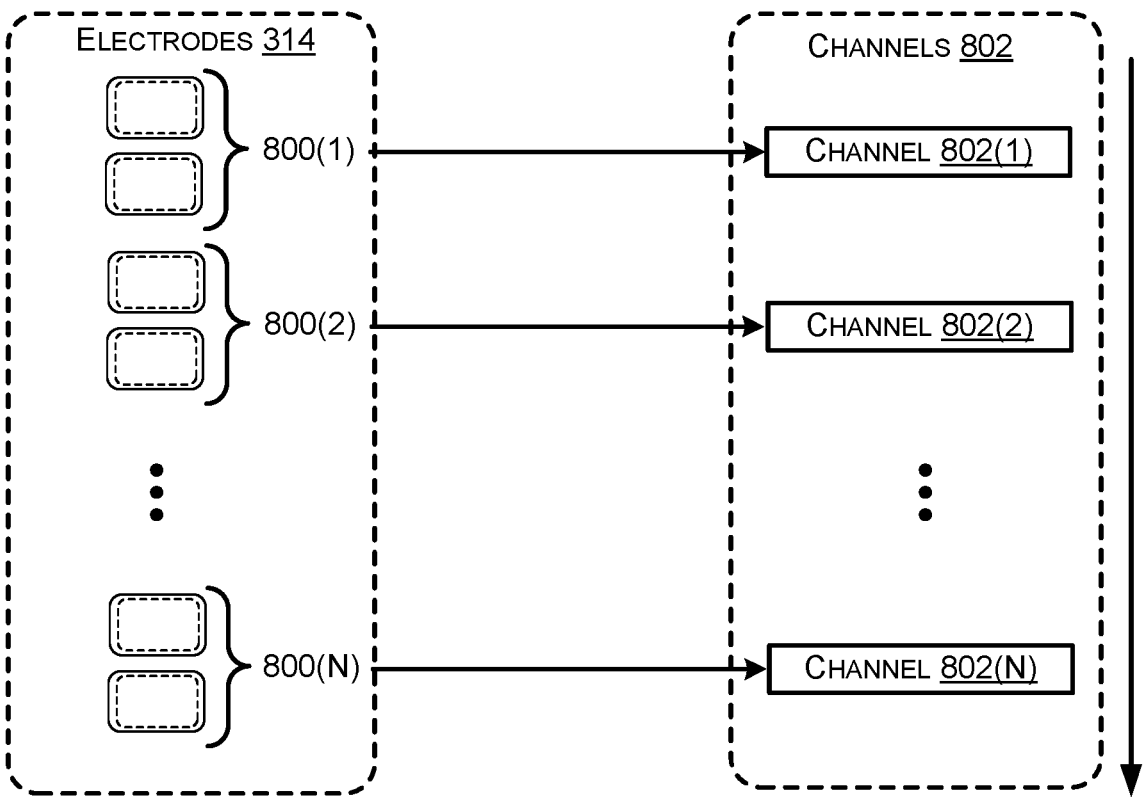
FIG. 8 illustrates a schematic diagram illustrating how pairs of electrodes correspond to channels for delivery of electrical impulses one channel after another.

FIG. 8 illustrates a schematic diagram illustrating how pairs 800 of electrodes 314 correspond to channels 802 for delivery of electrical impulses one channel 802 after another. One or more processors of the EMS suit 300, and/or of a system including the EMS suit 300, may cause circuitry of the EMS suit 300 to deliver electrical impulses to individual channels 802 of multiple channels 802(1)-(N) sequentially (or in the sequence), one channel 802 after another, and in accordance with pulse parameter settings 200 (e.g., intensity (amplitude), pulse width, etc.), "N" being any positive integer. In some embodiments, the number of channels 802 is equal to 13 channels (i.e., N=13). In other embodiments, the number of "N" channels may be implemented as a number "N" less than 13, or a number "N" greater than 13. During operation of the EMS suit 300, frames are processed at a frame rate. The frame rate (or frequency) may be set to a value in the pulse parameter settings 200. This frame rate may represent a frequency preset set by the manufacturer of the EMS suit 300. For a frame rate of 90 Hertz (Hz), output is serially provided across the N channels (e.g., where N=13) at a rate of 90 times per second. In other words, electrical impulses would be delivered to channels 802(1)-(N) sequentially (or in the sequence) during a frame, and this would occur 90 times a second (e.g., 90 frames processed in one second). For example, during a frame, a first electrical impulse (or pulse) may be delivered via the first pair of electrodes 800(1) corresponding to a first channel 802(1), followed by a second electrical impulse (or pulse) delivered via the second pair of electrodes 800(2) corresponding to a second channel 802(2), and so on and so forth for any suitable number of N channels. Because the number of channels 802 may be less than 13 channels, or greater than 13 channels, in some embodiments, it is to be appreciated that any number of electrodes 314 can be used, but, in general, there may be twice the number of electrodes 314 as there are channels 802. It is also to be appreciated that the ordering of electrode pairs 800 and channels 802 shown in FIG. 8 is nonlimiting in the present disclosure, and, therefore, it is to be appreciated that electrode pairs 800 can be fired in any suitable sequence, such as by ordering them differently relative to the ordering shown in FIG. 8.

Figure 9:
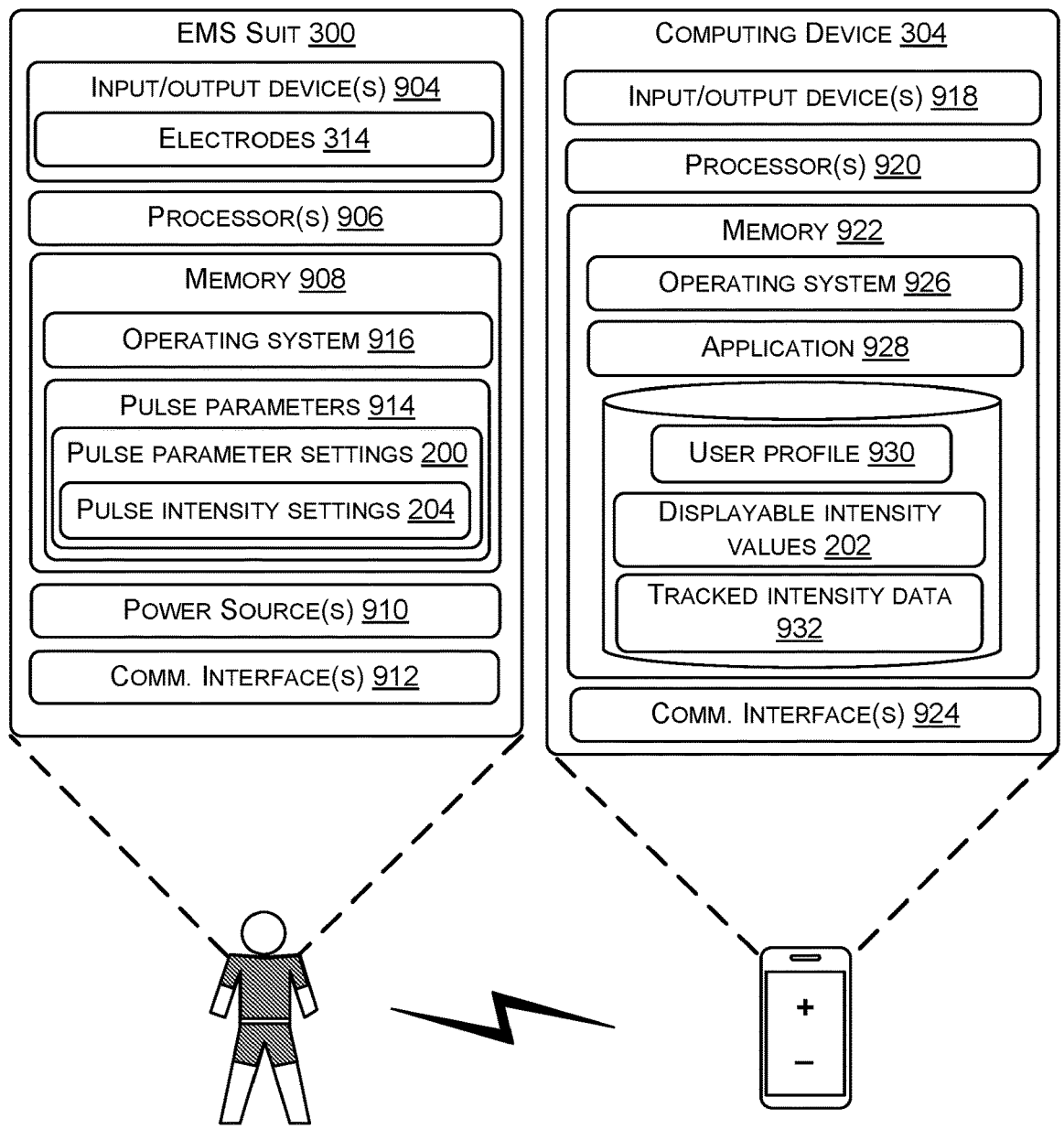
FIG. 9 illustrates block diagrams of a system that may include an EMS suit and a personal computing device, among other components/devices, according to embodiments described herein.

FIG. 9 illustrates block diagrams of a system 900 that may include an EMS suit 300 and a personal computing device 304, among other components/devices, according to embodiments described herein. The EMS suit 300 is shown as including one or more input/output (I/O) devices 904. For example, the I/O devices 904 may include one or more microphones to receive audio input, such as user voice input. In some implementations, one or more cameras or other types of sensors may function as input devices to receive gestural input and/or capture and interpret the user's posture and/or form. In some embodiments, additional input devices may be provided in the form of a keyboard, keypad, touch screen, control buttons and the like.

The output devices, meanwhile, may include the electrodes 314, as described herein, as well as display(s), light element (e.g., LED), a vibrator to create haptic sensations, a speaker(s) (e.g., headphones), and/or the like. With reference to the electrodes 314, electrical impulses (or pulses) may be delivered via the electrodes 314, which may be controlled via instructions received from a processor(s) of the system 900 (e.g., to control initiation, cessation, duration, channels 802, and/or intensity of the electrical impulses).

The EMS suit 300 is shown as including one or more processors 906, memory 908 (or non-transitory computer-readable media 908), power source(s) 910, and a communications interface(s) 912. In some implementations, the processors(s) 906 may include a central processing unit(s) (CPU(s)), a graphics processing unit(s) (GPU(s)), both CPU(s) and GPU(s), a microprocessor(s), a digital signal processor(s) or other processing units or components known in the art. Alternatively, or in addition, the functionally described herein can be performed, at least in part, by one or more hardware logic components. For example, and without limitation, illustrative types of hardware logic components that can be used include field-programmable gate arrays (FPGAs), application-specific integrated circuits (ASICs), application-specific standard products (ASSPs), system-on-a-chip systems (SOCs), complex programmable logic devices (CPLDs), etc. Additionally, each of the processor(s) 906 may possess its own local memory, which also may store program modules, program data, and/or one or more operating systems.

The memory 908 may include volatile and nonvolatile memory, removable and non-removable media implemented in any method or technology for storage of information, such as computer-readable instructions, data structures, program modules, or other data. The memory 908 may be implemented as computer-readable storage media ("CRSM"), which may be any available physical media accessible by the processor(s) 906 to execute instructions stored on the memory 908. In one basic implementation, CRSM may include random access memory ("RAM") and Flash memory. In other implementations, CRSM may include, but is not limited to, read-only memory ("ROM"), electrically erasable programmable read-only memory ("EEPROM"), compact disc (CD)-ROM, digital versatile disks (DVD) or other optical storage, magnetic cassettes, magnetic tape, magnetic disk storage or other magnetic storage devices, RAID storage systems, or any other tangible medium which can be used to store the desired information and which can be accessed by the processor(s) 906.

The power source(s) 910 may include one or more batteries, such as a battery pack. The power source(s) 910 may be removable and/or rechargeable. In some embodiments, the power source(s) 910 may include one or more solar panels. The communication interface(s) 912 may be configured to facilitate a wireless and/or wired connection to a network and/or to another device(s), such as a nearby computing device (e.g., a tablet or a mobile phone). An example is shown in FIG. 9 where the EMS suit 300 may be communicatively coupled to the computing device 304 via the communications interface(s) 912. For example, the processor(s) 906 may be configured to process computer-executable instructions and/or data received via the communications interface(s) 912 from the computing device 304 that cause the electrode(s) 304 to deliver an impulse(s) to one or more muscle group(s) in accordance with specified output parameters. Furthermore, adjustments to the output parameters (e.g., intensity adjustments, pulse width adjustment, etc.) made by a user 302 via the computing device 304 may be received via the communications interface(s) 912 and processed by the processor(s) 906 to adjust the output (e.g., the intensity of the electrical impulses) provided via the electrodes 314 and/or other output devices of the EMS suit 300. For example, the multiple electrodes 314 described herein may map to different muscle groups designated by respective channels 802 of an array of channels 802. For example, a first channel 802 may be designated for a pair of electrodes 800 on the pants portion 308, a second channel 802 for a pair of electrodes 800 on the vest portion 306, a third channel 802 for a pair of electrodes 800 on an arm band 310, and so on and so forth, where each portion 306/308/310 can have multiple pairs of electrodes 800. The electrodes 314 of the example EMS suit 300 shown in FIG. 3, for example, may map to a total of N channels (e.g., N=13 channels), where each channel 802 controls electrical impulse delivery of a given pair of electrodes 800.

The electrical impulse intensity for these respective channels 802 may be adjustable independent of the other channels 802, and each channel 802 may be independently operated (e.g., electrical impulses may be delivered via electrodes 314 positioned on the legs of the user, without eliciting muscle contraction of the user's upper body at all). Therefore, muscle groups can be isolated to contract particular targeted muscles, and the intensities of each channel 802 may be set at relative levels (e.g., less intense on the legs, more intense on the arms, etc.). Thus, relative, per-channel 802 (or per-muscle group) settings of intensity levels can be maintained in the pulse parameter settings 200 of the pulse parameters 914, and the adjustments made by the user may increase or decrease at least some of these parameters 914. Additionally, or alternatively, a global intensity value (or level) 104 may be adjusted by a user to increase or decrease the intensity across all channels with a single adjustment, as described herein. Additionally, or alternatively, a channel subset intensity value (or level) 430/444 may be adjusted by a user to increase or decrease the intensity across particular subsets of channels with a single adjustment, as described herein. Furthermore, the arrangement of the electrodes 314 on the EMS suit 300 may allow for one-sided delivery of electrical impulses (e.g., to one side of the body or the other, relative to the midsagittal plane of the body). That is, if the user has an injury on his/her right arm, or if the user is an amputee with only a left arm, the EMS suit 300 may be controlled to deliver electrical impulses to a channel 802(2) for the left arm, without delivering electrical impulses to a channel 802(1) for the right arm.

The pulse intensities for the respective channels 802 may also be adjustable independent of the other channels 802. Therefore, the pulse intensities (or channel intensity values 206) of each channel 802 may be set at relative levels by adjusting the channel-specific intensity values 218 associated with the respective channels 802, by adjusting the channel subset intensity values 430/444 associated with respective subsets of channels 802, and/or by adjusting the global intensity value 104 associated with the complete set of channels 802. Thus, relative, per-channel 802 (or per-muscle group) settings of values 206 for pulse intensities can be maintained in the pulse intensity settings 204, and the adjustments made by the user may increase or decrease at least some of these pulse intensity parameters. In general, the pulse parameter settings 200 may be stored in memory of a system including the EMS suit 300, such as in the memory 908. The pulse parameter settings 200 may correspond to pulse parameter presets that were set by a manufacturer of the EMS suit 300. After adjustment, however, such as when the user 302 adjusts the presets, or when the presets are adjusted programmatically, the adjusted pulse parameter settings 200 may correspond to adjusted values different than the presets.

The communication interface(s) 912 may implement multiple types of wireless or radio technologies, such as a radio that is configured to operate as a Bluetooth radio (e.g., Bluetooth Low Energy (BLE) radio), a Wi-Fi radio, a cellular radio, and/or combinations thereof. Therefore, in at least some embodiments, the communication interface(s) 912 may comprise a wireless communication interface (e.g., wireless radio). It is to be appreciated that the communication interface(s) 912 may further include physical ports to facilitate a wired connection to a network, a connected peripheral device, or a plug-in network device that communicates with other wireless networks. In any case, the communications interface(s) 912 may allow for receiving commands from a nearby computing device(s) (e.g., the computing device 304) to control an aspect of output provided by the EMS suit 300. For example, a command may be received wirelessly via the communication interface(s) 912 to control the initiation of an electrical impulse(s), the cessation of an electrical impulse(s), or adjustment of an intensity, a pulse width, etc., of an electrical impulse(s) delivered via an electrode(s) 314 of the EMS suit 300.

Several modules such as instruction, datastores, and so forth may be stored within the memory 908 and configured to execute on the processor(s) 906. An operating system module 916 may be configured to manage hardware within and coupled to the EMS suit 300 for the benefit of other modules, for example. The memory 908 may further store pulse parameters 914, including pulse parameter settings 200, such as pulse intensity settings 204, that are used to control the output of the electrodes 314. It is to be appreciated that some or all of the pulse parameters 914, including some or all of the pulse parameter settings 200, such as pulse intensity settings 204, may be stored in other memory of the system 900, such as memory 922 of the computing device 304. An electrical impulse that is delivered via any electrode pair 800, as described herein, may include individual pulses of electrical energy. In some embodiments, the processor(s) 906 of the EMS suit 300 is configured to deliver electrical impulses sequentially over multiple channels 802 to allow for serialized delivery of electrical impulses per electrode pair 800, as described herein. Accordingly, electrical impulse delivery may occur sequentially, channel-by-channel, one channel 802 after another. Pulse parameters 914 (or attributes) of electrical impulses delivered via electrodes 314 of the EMS suit 200 may include, without limitation, pulse width (or pulse duration), frequency/frame rate (e.g., the number of pulses per second, measured in Hz), inter-pulse interval (e.g., the time between individual pulses, or an "OFF time"), phase width (e.g., the duration of one phase of the pulse, or an "ON time"), interphase interval (e.g., the time between phases of a pulse), pulse intensity (amplitude), ramp up time (e.g., the time it takes for the current intensity to increase from zero to its target intensity), plateau time (e.g., the time during which the pulse remains at a maximum intensity), and/or ramp down time (e.g., the time it takes for the current intensity to decrease from its target intensity to zero).

As shown in FIG. 9, the computing device 304 may include one or more input/output (I/O) devices 918, such as the controls (e.g., joysticks, trackpads, triggers, depressible buttons, etc.), potentially any other type of input or output devices. For example, the I/O devices 918 may include one or more microphones to receive audio input, such as user voice input. In some implementations, one or more cameras or other types of sensors may function as input devices to receive gestural input, such as motion of the computing device 304. In some embodiments, additional input devices may be provided in the form of a keyboard, keypad, mouse, touch screen, joystick, control buttons, motion sensors, accelerometer(s), gyroscope(s), inertial measurement unit(s) (IMU(s)), and the like. The input device(s) may further include control mechanisms, such as basic volume control button(s) for increasing/decreasing volume, as well as power and reset buttons.

The output devices, meanwhile, may include a display(s), a light element (e.g., LED), a vibrator to create haptic sensations, a speaker(s) (e.g., headphones), and/or the like. While a few examples have been provided, the computing device 304 may additionally or alternatively comprise any other type of output device. In some instances, output by the one or more output devices may be based on input received by one or more of the input devices. For example, actuation of a control or the touchscreen may result in the output of a haptic response by a vibrator located adjacent (e.g., underneath) the control, the touchscreen, or at any other location.

The computing device 304 is shown as including one or more processors 920, memory 922 (or non-transitory computer-readable media 922), and a communications interface(s) 924. These components may be implemented similarly to the processor(s) 906, memory 908, and communication interface(s) 912 described with reference to the EMS suit 300, and, as such, details of these components will not be explained again for the sake of brevity, as the description of the processor(s) 906, memory 908, and communication interface(s) 912 may be referenced herein to understand example implementations of the processor(s) 920, memory 922, and communication interface(s) 924.

Several modules such as instruction, datastores, and so forth may be stored within the memory 922 and configured to execute on the processor(s) 920. A few example functional modules are shown as stored in the memory 922 and executed on the processor(s) 920, although the same functionality may alternatively be implemented in hardware, firmware, or as a SOC.

An operating system module 926 may be configured to manage hardware within and coupled to the computing device 304 for the benefit of other modules. In addition, the memory 922 may store a client application 928, which may represent an executable application (e.g., code, computer-executable instructions, etc.) that is configured to decode media data and/or command data, to playback the media data (e.g., a video of an instructor performing a workout session), to process command data, to generate and send commands to the EMS suit 300 based at least in part on the command data, and/or to cause presentation of GUIs, such as the GUIs 100, 400A-E illustrated in FIGS. 1 and 4A-E, for adjusting pulse parameter settings 200, or graphical overlays that are presented atop media content 102 based at least in part on the command data. The client application 928 may provide a user interface for a user to initiate playback of media data (e.g., a video file(s)) representing a workout session conducted by an instructor, for example. The user can provide user input (e.g., select a button, such as a physical button on the device or a soft button (e.g., a "play" icon) on a touch screen), issue a voice command, etc.) to start playback of the media data or to start the workout session when the user is ready to start, and/or the user may adjust the output of the EMS suit 300 via a user interface (e.g., a GUI) of the computing device 304 (e.g., via a touchscreen). The memory 922 may further include a data store, which may store one or more user profiles 930, such as a user profile 930 of a user who has logged into the client application 928 in the past, as well as media data and/or command data generated by the computing device 304 or received (e.g., downloaded) from a remote system over a wide area network (e.g., the Internet).

The data store may further include displayable intensity values 202, such as the channel-specific intensity values 208, channel subset intensity values, and/or the global intensity value 104 described herein, which are displayable via a GUI on the device 304, and/or which may be casted to a peripheral system 318 for display thereon. The data store may further include tracked intensity data 932, such as histories of intensity values 502 (or intensity profiles, curves, etc.), values corresponding to areas under curves 502 representing histories of intensity values, performance scores, and the like. This tracked intensity data 932 may be uploaded and/or downloaded to/from a remote system over a wide area network (e.g., the Internet) at multiple different times, such as at the start of a workout session, after completion of a workout session, in real-time as intensity values are tracked, periodically, in response to user input, etc. As such, tracked intensity data 932 may be synched to/from the "cloud" for maintaining a performance history of a user in association with the user profile 930 of the user 302.

It is to be appreciated that some or all of the components shown in FIG. 9, with the exception of the electrodes 314, may be provided in an impulse pack 312 situated in or on the EMS suit 300. Furthermore, the electrodes 314 may be coupled to the processor(s) 906 via electrical wires (or wirelessly), and the EMS suit 300 may be communicatively coupled to the processor(s) 920 of the computing device 304. Furthermore, a layer of base material (e.g., an undergarment) may be worn between the electrode(s) 314 and the skin of the user. In some embodiments, gel and/or water and/or similar materials may be interposed between the electrode(s) 314 and the base layer of material to improve electrical conductivity.

Figure 10:
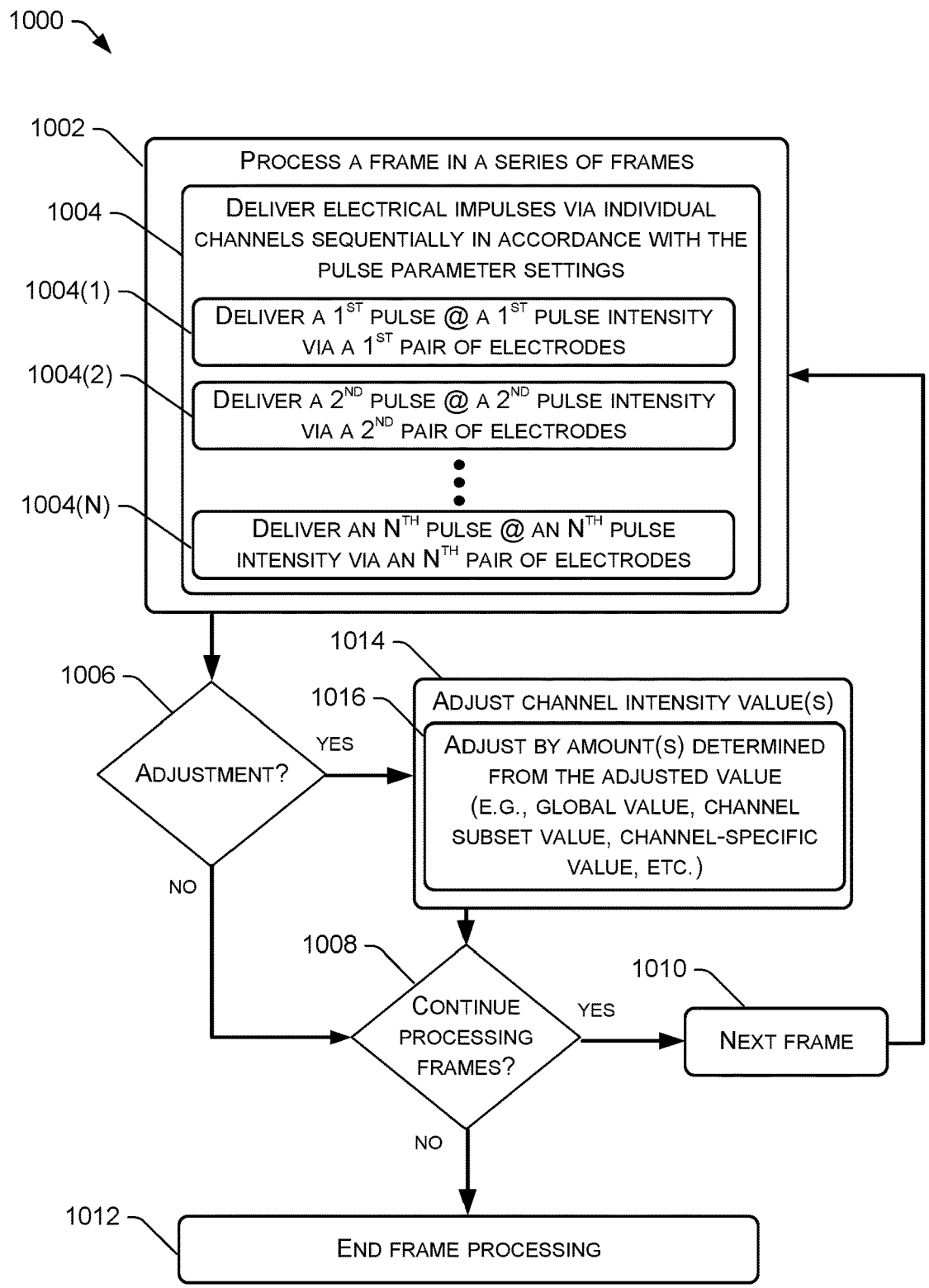
FIG. 10 is a flow diagram of an example process for controlling an EMS suit to deliver electrical impulses at respective pulse intensities and for adjusting the intensities during operation of the EMS suit, according to embodiments described herein.

FIG. 10 is a flow diagram of an example process 1000 for controlling an EMS suit 300 to deliver electrical impulses at respective pulse intensities and for adjusting the intensities during operation of the EMS suit 300, according to embodiments described herein. For discussion purposes, the process 1000 is described with reference to the previous figures.

At 1002, a processor(s) (e.g., the processor(s) 906 and/or the processor(s) 920) may process a frame of the series of frames, which causes delivery of electrical impulses via multiple electrodes 314 of an EMS suit 300. For example, the processor(s) may process a series of frames, and, during each frame, at 1002, the processor(s) may control the electrodes 314 of the EMS suit 300 to deliver electrical impulses in accordance with the pulse parameter settings 200 for the EMS suit 300. The electrical impulses delivered via electrodes 314 of the EMS suit 300 may elicit muscle contraction of a user 302 wearing the EMS suit 300. A frame rate (or frequency) at which the series of frames may be processed can be any suitable frame rate, such as a frame rate within a range of about 1-120 Hz. This frequency setting may be set in the pulse parameter settings 200, and it may represent a frequency preset that was set by the manufacturer of the EMS suit 300. A given frame, of a series of frames, may be processed at block 1002 during a workout session while a user 302 is using the EMS suit 300. Block 1004 may represent a sub-operation(s) of block 1002 during the processing of a frame.

At 1004, the processor(s) (e.g., the processor(s) 906 and/or the processor(s) 920) may cause circuitry of the EMS suit 300 to deliver electrical impulses to individual channels 802 of multiple (N) channels 802 sequentially (or in the sequence), one channel 802 after another, and in accordance with the pulse parameter settings 200 (e.g., pulse intensity settings 204). For example, at 1004(1), a first electrical pulse may be delivered via a first pair of electrodes 800(1) corresponding to a first channel 802(1), the first electrical pulse having a first pulse intensity. At 1004(2), following block 1004(1), a second electrical pulse may be delivered via a second pair of electrodes 800(2) corresponding to a second channel 802(2), the second electrical pulse having a second pulse intensity. This may continue during the processing of a frame for any suitable number of N channels 802 until, at 1004(N), an $N^{th}$ electrical pulse is delivered via an $N^{th}$ pair of electrodes 800(N) corresponding to an $N^{th}$ channel 802(N), the $N^{th}$ electrical pulse having an $N^{th}$ pulse intensity.

The pulse intensities may be determined by referencing the pulse intensity settings 204 for the EMS suit 300, which may be stored in memory (e.g., the memory 908 and/or the memory 922). For example, as shown in FIG. 2, the pulse intensity settings 204 may comprise, or specify, multiple channel intensity values 206 including a first value (e.g., 15 mA) associated with a first channel 802(1) (e.g., Channel 1), a second value (e.g., 15 mA) associated with a second channel 802(2) (e.g., Channel 2), a third value (e.g., 15 mA) associated with a third channel 802(3) (e.g., Channel 3), and so on and so forth for any number of N channels. The intensity can be uniform across all channels 802 (e.g., Channels 1-N), or the intensity can vary one or more channels.

At block 1006, the processor(s) (e.g., the processor(s) 906 and/or the processor(s) 920) may determine whether an adjustment has been made. For example, the determination at block 1006 may be to determine whether an intensity adjustment control 106 has been selected on a touchscreen. As described herein, other forms of user input can be detected for adjusting the intensity, such as voice input, gestural input, etc. If no adjustment has been made, the process 1000 may follow the "NO" route from block 1006 to block 1008.

At block 1008, the processor(s) (e.g., the processor(s) 906 and/or the processor(s) 920) may determine whether to continue processing frames of the series of frames. If a next frame is to be processed, the process 1000 may follow the "YES" route from block 1008 to block 1010 by transitioning to the next frame, and by processing the next frame in the series of frames at block 1002. If a next frame is not to be processed, the process 1000 may end frame processing at block 1012 by following the "NO" route from block 1008 to block 1012. For example, if an end of a workout session has been reached, the processor(s) (e.g., the processor(s) 906 and/or the processor(s) 920) may determine to end frame processing at block 1012 so that the user can remove the EMS suit 300 from his/her body.

Returning to block 1006, if an adjustment has been made, the process 1000 may follow the "YES" route from block 1006 to block 1014. For example, the processor(s) may, at block 1006, determine that at least one of the first intensity adjustment control 106(1) or the second intensity adjustment control 106(2) has been selected.

At block 1014, the processor(s) may adjust a channel intensity value(s) 206 to an adjusted channel intensity value(s) 206. The amount(s) by which the channel intensity value(s) 206 is adjusted may depend on the state that the GUI is in at the time when the adjustment is detected. For example, the user 302 may adjust the global intensity value 104, a channel subset intensity value 430/440, or a channel-specific intensity value 218.

At block 1016, the processor(s) may adjust, in the pulse intensity settings 204, respective ones of the one or more channel intensity values 206 by respective amounts that are determined based at least in part on the adjusted intensity value to obtain one or more adjusted channel intensity values 206. For example, if the adjustment detected at block 1006 is an adjustment to the global intensity value 104, respective ones of the multiple channel intensity values 206 (e.g., the complete set of N channel intensity values 206) may be adjusted by respective amounts that are determined based at least in part on the adjusted global intensity value 104 to obtain multiple adjusted channel intensity values 206. As another example, if the adjustment detected at block 1006 is an adjustment to a channel subset intensity value 430/444, respective ones of the multiple channel intensity values 206 (e.g., a corresponding subset of the N channel intensity values 206) may be adjusted by respective amounts that are determined based at least in part on the adjusted channel subset intensity value 430/444 to obtain multiple adjusted channel intensity values 206. As yet another example, if the adjustment detected at block 1006 is an adjustment to a channel-specific intensity value 218 (or, "displayable channel intensity value 218"), a channel intensity value 206 (e.g., a single corresponding channel intensity value 206) may be adjusted by an amount that is determined based at least in part on the adjusted channel-specific intensity value 218 to obtain an adjusted channel intensity value 206. As described in detail above, the multiple channel intensity values 206 may represent milliamps (mA) of electrical current, and each displayable channel intensity value 218 (or "channel-specific intensity value 218") may be adjustable in increments between a minimum value and a maximum value, and each increment of the increments may correspond to a fraction of a mA. Therefore, the amount of adjustment to the channel intensity value(s) 206 can be determined at block 1016 based on this mathematical relationship.

Following the adjustment at block 1014, the process 1000 may proceed to block 1008, and then to either block 1010 or 1012. If another frame is to be processed, the next frame is processed at block 1002 to cause subsequent electrical impulses to be delivered via the multiple electrodes 314 of the EMS suit 300 at one or more respective adjusted intensities based at least in part on the adjusted channel intensity value(s) 206 adjusted at block 1014.

Figure 11:
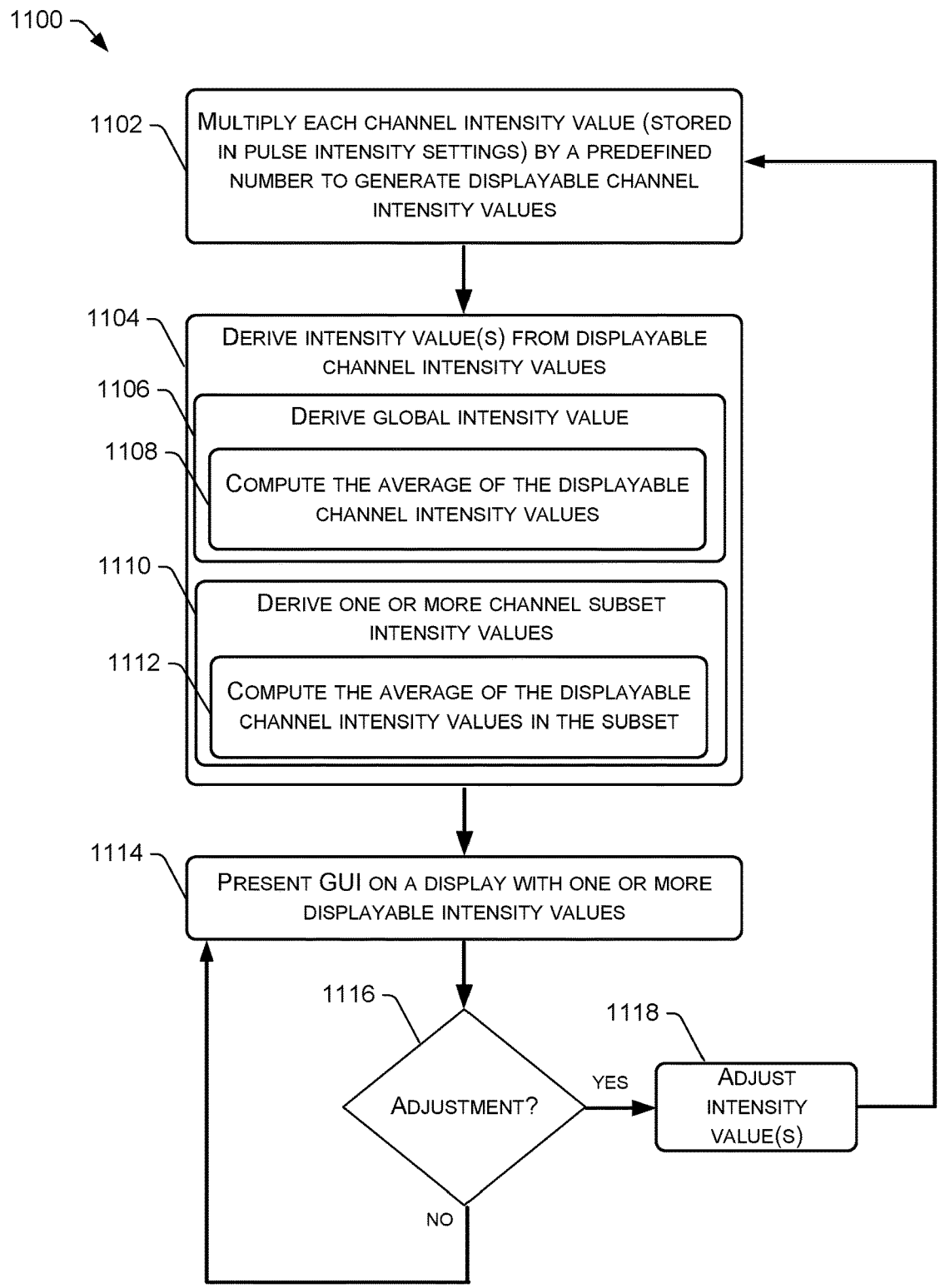
FIG. 11 is a flow diagram of an example process for formulating and displaying intensity values via a GUI during operation of the EMS suit, according to embodiments described herein

FIG. 11 is a flow diagram of an example process 1100 for formulating and displaying intensity values via a GUI during operation of the EMS suit 300. For discussion purposes, the process 1100 is described with reference to the previous figures.

At 1102, a processor(s) (e.g., the processor(s) 906 and/or the processor(s) 920) may multiply each channel intensity value 206 of the multiple channel intensity values (which are stored in the pulse intensity settings 204 for an EMS suit 300) by a predefined number to generate displayable channel intensity values 218. For example, each channel intensity value 206 may be multiplied by the number "4" to derive the displayable channel intensity values 218 that are specific to each channel 802 of multiple channels.

At 1104, the processor(s) may derive one or more intensity values from the displayable channel intensity values generated at block 1102. For example, at sub-block 1106, the processor(s) may derive a global intensity value 104 from the displayable channel intensity values 218. For example, at sub-block 1108, the processor(s) may compute the average of the displayable channel intensity values 218 to derive the global intensity value 104, although any other statistical computation can be implemented. As another example, at sub-block 1110, the processor(s) may derive one or more channel subset intensity values 430/444 from the displayable channel intensity values 218. For example, at sub-block 1112, the processor(s) may compute the average of a particular subset(s) of the displayable channel intensity values 218 to derive the channel subset intensity value(s) 430/444, although any other statistical computation can be implemented. In an illustrative example, a subset of channels 802 may correspond to the pants portion 308 of the EMS suit 300. Accordingly, the average of the subset of the displayable channel intensity values 218 associated with the pants portion 308 may be computed at block 1112 to derive the channel subset intensity value 444 associated with the pants portion 308 of the EMS suit 300.

At 1114, the processor(s) may present a GUI on a display with one or more displayable intensity values. For example, the processor(s) may present the global intensity value 104 on the display (e.g., via the GUI 100 of FIG. 1). As another example, the processor(s) may present a channel subset intensity value, such as the value 430 via the GUI 400B or the value 444 via the GUI 400C. As yet another example, the processor(s) may present a channel-specific intensity value 218 (or, "displayable channel intensity value 218") via the GUI 400D. It is also to be appreciated that the operation(s) performed at block 1114 may include the operations described with reference to the processes 402, 414, 432, and/or 446. In this sense, the presentation of the GUI at block 1114 may involve presenting an interactive GUI that the user may interact with to dynamically modify the elements presented on the GUI at any given time.

At 1116, the processor(s) may determine whether an adjustment has been made. For example, the determination at block 1116 may be to determine whether an intensity adjustment control 106 has been selected on a touchscreen. As described herein, other forms of user input can be detected for adjusting the intensity, such as voice input, gestural input, etc. If no adjustment has been made, the process 1100 may follow the "NO" route from block 1116 to block 1114 where the GUI can remain presented with the same displayable intensity values. If, however, an adjustment has been made at block 1116, the process 1100 may follow the "YES" route from block 1116 to block 1118. For example, the processor(s) may, at block 1116, determine that at least one of the first intensity adjustment control 106(1) or the second intensity adjustment control 106(2) has been selected.

At block 1118, the processor(s) may adjust the appropriate intensity value on the GUI to an adjusted intensity value. For example, if the global intensity value 104 is presented at the time of the adjustment, the processor(s) may adjust the global intensity value 104 to an adjusted global intensity value. As another example, if a channel subset intensity value 430/444 is presented at the time of the adjustment, the processor(s) may adjust the channel subset intensity value 430/444 to an adjusted channel subset intensity value. As yet another example, if a channel-specific intensity value 218 is presented at the time of the adjustment, the processor(s) may adjust the channel-specific intensity value 218.

After the adjustment at block 1118, the adjusted intensity value may be presented by iterating blocks 1102-1114. That is, the amount of adjustment to the channel intensity value(s) 206 can be determined using the process 1000 of FIG. 10, and upon setting the adjusted channel intensity values 206 in the pulse intensity settings 204, the displayable intensity values 202 can be derived using the process 1100 to present the adjusted intensity value (e.g., the adjusted global intensity value 104, the adjusted channel subset intensity value 430/444, or the adjusted channel-specific intensity value 218).

Unless otherwise indicated, all numbers expressing quantities used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

The environment and individual elements described herein may of course include many other logical, programmatic, and physical components, of which those shown in the accompanying figures are merely examples that are related to the discussion herein.

Other architectures may be used to implement the described functionality, and are intended to be within the scope of this disclosure. Furthermore, although specific distributions of responsibilities are defined above for purposes of discussion, the various functions and responsibilities might be distributed and divided in different ways, depending on circumstances.

Furthermore, although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

Although the subject matter has been described in language specific to structural features and/or methodological acts, it is to be understood that the subject matter defined in the appended claims is not necessarily limited to the specific features or acts described. Rather, the specific features and acts are disclosed as illustrative forms of implementing the claims.

What is claimed is:

1. A system comprising:
   a processor;
   a display;
   an electrical muscle stimulation (EMS) suit having multiple electrodes, wherein individual pairs of the multiple electrodes correspond to individual channels of multiple channels for delivering electrical impulses via the multiple electrodes; and
   memory storing:
      pulse intensity settings comprising multiple channel intensity values associated with the multiple channels; and
      computer-executable instructions that, when executed by the processor, cause the system to perform operations comprising:
         delivering the electrical impulses via the multiple electrodes at respective intensities based at least in part on the multiple channel intensity values;
         multiplying each channel intensity value of the multiple channel intensity values by a predefined number to generate displayable channel intensity values;
         deriving a global intensity value from the displayable channel intensity values; and
         presenting the global intensity value on the display.

2. The system of claim 1, the operations further comprising presenting on the display media content featuring an instructor conducting a workout session, wherein the presenting of the global intensity value comprises presenting the global intensity value as a graphic overlaying the media content on the display.

3. The system of claim 1, the operations further comprising:
   presenting on the display a first intensity adjustment control and a second intensity adjustment control;
   determining that at least one of the first intensity adjustment control or the second intensity adjustment control has been selected;
   adjusting the global intensity value to an adjusted global intensity value;
   presenting the adjusted global intensity value on the display;

adjusting, in the pulse intensity settings, respective ones of the multiple channel intensity values by respective amounts that are determined based at least in part on the adjusted global intensity value to obtain multiple adjusted channel intensity values; and delivering subsequent electrical impulses via the multiple electrodes at respective adjusted intensities based at least in part on the multiple adjusted channel intensity values.

4. The system of claim 1, wherein:
the multiple channel intensity values represent milliamps of electrical current;
each displayable channel intensity value is adjustable in increments between a minimum value and a maximum value; and
each increment of the increments corresponds to a fraction of a milliamp.

5. The system of claim 1, the operations further comprising:
presenting on the display:
a channel intensity adjustment element;
a first intensity adjustment control; and
a second intensity adjustment control;
determining that the channel intensity adjustment element has been selected;
presenting on the display, in response to the determining, multiple channel identifier elements identifying the multiple channels;
determining that a channel identifier element of the multiple channel identifier elements has been selected;
presenting on the display a displayable channel intensity value of the displayable channel intensity values corresponding to a channel identified by the channel identifier element;
determining that at least one of the first intensity adjustment control or the second intensity adjustment control has been selected;
adjusting the displayable channel intensity value to an adjusted displayable channel intensity value;
presenting the adjusted displayable channel intensity value on the display;
adjusting, in the pulse intensity settings, a channel intensity value of the multiple channel intensity values by an amount that is determined based at least in part on the adjusted displayable channel intensity value to obtain an adjusted channel intensity value; and
delivering subsequent electrical impulses via the multiple electrodes at respective adjusted intensities based at least in part on the adjusted channel intensity value.

6. The system of claim 1, the operations further comprising:
presenting on the display:
a channel intensity adjustment element;
a first intensity adjustment control; and
a second intensity adjustment control;
determining that the channel intensity adjustment element has been selected;
presenting on the display, in response to the determining:
multiple channel identifier elements identifying the multiple channels; and
multiple suit portion elements identifying multiple portions of the EMS suit;
determining that a suit portion element of the multiple suit portion elements has been selected;
presenting on the display a channel subset intensity value derived from a subset of the displayable channel intensity values corresponding to channels associated with a portion of the EMS suit identified by the suit portion element;
determining that at least one of the first intensity adjustment control or the second intensity adjustment control has been selected;
adjusting the channel subset intensity value to an adjusted channel subset intensity value;
presenting the adjusted channel subset intensity value on the display;
adjusting, in the pulse intensity settings, respective ones of the multiple channel intensity values by respective amounts that are determined based at least in part on the adjusted channel subset intensity value to obtain multiple adjusted channel intensity values; and
delivering subsequent electrical impulses via the multiple electrodes at respective adjusted intensities based at least in part on the multiple adjusted channel intensity values.

7. The system of claim 1, wherein the delivering of the electrical impulses occurs during a workout session, the operations further comprising:
presenting on the display, during the workout session, a pre-programmed sequence of global intensity values plotted over time;
adjusting the global intensity value during the workout session based at least in part on the pre-programmed sequence; and
presenting on the display, during the workout session, a history of global intensity values resulting from the adjusting.

8. The system of claim 7, the operations further comprising:
presenting on the display a global intensity stabilizer element;
determining that the global intensity stabilizer element has been selected;
overriding the pre-programmed sequence with instructions to fix the global intensity value at a current value for a remainder of the workout session; and
presenting on the display a modified pre-programmed sequence of global intensity values plotted over time indicating that the global intensity value will remain fixed at the current value for the remainder of the workout session or until the global intensity stabilizer element is subsequently selected.

9. A method comprising:
delivering electrical impulses via multiple electrodes of an electrical muscle stimulation (EMS) suit in accordance with pulse intensity settings, the pulse intensity settings comprising multiple channel intensity values associated with multiple channels;
multiplying each channel intensity value of the multiple channel intensity values by a predefined number to generate displayable channel intensity values;
deriving a global intensity value from the displayable channel intensity values; and
presenting the global intensity value on a display.

10. The method of claim 9, further comprising presenting on the display media content featuring an instructor conducting a workout session, wherein the presenting of the global intensity value comprises presenting the global intensity value as a graphic overlaying the media content on the display.

11. The method of claim 9, further comprising:
determining, based at least in part on detected user input, to adjust the global intensity value;

adjusting the global intensity value to an adjusted global intensity value based at least in part on the user input;
presenting the adjusted global intensity value on the display;
adjusting, in the pulse intensity settings, respective ones of the multiple channel intensity values by respective amounts that are determined based at least in part on the adjusted global intensity value to obtain multiple adjusted channel intensity values; and
delivering subsequent electrical impulses via the multiple electrodes at respective adjusted intensities based at least in part on the multiple adjusted channel intensity values.

12. The method of claim 9, wherein the delivering of the electrical impulses occurs during a workout session, the method further comprising:
adjusting the global intensity value during the workout session;
presenting on the display, during the workout session:
a first history of global intensity values resulting from the adjusting, the first history of global intensity values associated with a user of the EMS suit; and
a second history of global intensity values associated with at least one of:
a previous workout session performed by the user; or
another user who is performing, or has performed, the workout session while using another EMS suit.

13. The method of claim 9, wherein the delivering of the electrical impulses occurs during a workout session, the method further comprising:
adjusting the global intensity value during the workout session;
plotting, as a curve on a graph, a history of global intensity values resulting from the adjusting;
determining a value corresponding to an area under the curve;
determining a performance score of a user of the EMS suit based at least in part on the value; and
providing the user with access to the performance score.

14. The method of claim 9, wherein the delivering of the electrical impulses occurs during a workout session, the method further comprising:
adjusting the global intensity value during the workout session;
plotting, as a curve on a graph, the history of global intensity values resulting from the adjusting;
determining a value corresponding to an area under the curve; and
determining a starting global intensity value for a subsequent workout session based at least in part on the value.

15. One or more non-transitory computer-readable media storing computer-executable instructions that, when executed by one or more processors, cause performance of operations comprising:
delivering electrical impulses via multiple electrodes of an electrical muscle stimulation (EMS) suit in accordance with pulse intensity settings, the pulse intensity settings comprising multiple channel intensity values associated with multiple channels;
multiplying each channel intensity value of the multiple channel intensity values by a predefined number to generate displayable channel intensity values;
deriving a global intensity value from the displayable channel intensity values; and
presenting the global intensity value on a display.

16. The one or more non-transitory computer-readable media of claim 15, the operations further comprising:
adjusting the global intensity value during multiple workout sessions; and
storing a history of global intensity values resulting from the adjusting.

17. The one or more non-transitory computer-readable media of claim 16, the operations further comprising presenting on the display a multi-session intensity profile as a sequence of at least some global intensity values of the history of global intensity values plotted over time.

18. The one or more non-transitory computer-readable media of claim 15, the operations further comprising:
presenting on the display a first intensity adjustment control and a second intensity adjustment control;
determining that at least one of the first intensity adjustment control or the second intensity adjustment control has been selected;
adjusting the global intensity value to an adjusted global intensity value;
presenting the adjusted global intensity value on the display;
adjusting, in the pulse intensity settings, respective ones of the multiple channel intensity values by respective amounts that are determined based at least in part on the adjusted global intensity value to obtain multiple adjusted channel intensity values; and
delivering subsequent electrical impulses via the multiple electrodes at respective adjusted intensities based at least in part on the multiple adjusted channel intensity values.

19. The one or more non-transitory computer-readable media of claim 15, wherein:
the multiple channel intensity values represent milliamps of electrical current;
each displayable channel intensity value is adjustable in increments between a minimum value and a maximum value; and
each increment of the increments corresponds to a fraction of a milliamp.

20. The one or more non-transitory computer-readable media of claim 15, the operations further comprising presenting on the display media content featuring an instructor conducting a workout session, wherein the presenting of the global intensity value comprises presenting the global intensity value as a graphic overlaying the media content on the display.

* * * * *